US012580067B2

(12) United States Patent
    Joshi

(10) Patent No.: US 12,580,067 B2
(45) Date of Patent: *Mar. 17, 2026

(54) SYSTEM AND METHOD FOR DISPENSING A CUSTOMIZED NUTRACEUTICAL PRODUCT

(71) Applicant: Supplement Technology Limited, Stockport (GB)

(72) Inventor: Jatin Joshi, London (GB)

(73) Assignee: Supplement Technology Limited, Stockport (GB)

( * ) Notice: Subject to any disclaimer, the term of this patent is extended or adjusted under 35 U.S.C. 154(b) by 138 days.

This patent is subject to a terminal disclaimer.

(21) Appl. No.: 18/225,663

(22) Filed: Jul. 24, 2023

(65) Prior Publication Data

US 2024/0062873 A1    Feb. 22, 2024

Related U.S. Application Data

(63) Continuation-in-part of application No. 17/108,928, filed on Dec. 1, 2020, now Pat. No. 11,710,551.

(51) Int. Cl.
    *G16H 20/60* (2018.01)
    *G06N 20/00* (2019.01)
    (Continued)

(52) U.S. Cl.
    CPC .............. *G16H 20/60* (2018.01); *G06N 20/00* (2019.01); *G06Q 10/08* (2013.01); *G06Q 10/087* (2013.01);
    (Continued)

(58) Field of Classification Search
    CPC ...... G16H 20/60; G06Q 10/08; G06Q 10/087; G06Q 30/0621
    (Continued)

(56) References Cited

U.S. PATENT DOCUMENTS

| | | | |
|---|---|---|---|
| 2002/0004749 A1* | 1/2002 | Froseth ................. | G06Q 50/00 705/16 |
| 2014/0236359 A1* | 8/2014 | Minvielle .............. | G16H 20/60 700/275 |

(Continued)

FOREIGN PATENT DOCUMENTS

| | | | | |
|---|---|---|---|---|
| KR | 20210018619 A | * | 2/2021 | ............. G16H 20/60 |

OTHER PUBLICATIONS

Roanes-Lozano, Eugenio et al.; A prototype of a RBES for personalized menus generation; Applied Mathematics and Computation 315 : 615-624. Elsevier Inc. (Sep. 29, 2016) (Year: 2016).*

*Primary Examiner* — Hiep V Nguyen
(74) *Attorney, Agent, or Firm* — Holland & Hart LLP

(57) ABSTRACT

A system (100) and method (900) for dispensing a personalized nutraceutical (81) to a consumer (62). The system (100) can create the personalized nutraceutical (81) that is selectively influenced by one or more health attributes (640) relating to the intended consumer (62) of the personalized nutraceutical (81). The application(s) (373) of the system (300) can create a variety of outputs (690) including a personalized recipe (693) for the personalized nutraceutical (81) from a variety of inputs (610) that can include the health attributes (640) of the consumer (62). A production assembly (500) can manufacture the personalized nutraceutical (81) using the personalized recipe (693).

21 Claims, 21 Drawing Sheets

(51) Int. Cl.
*G06Q 10/08* (2024.01)
*G06Q 10/087* (2023.01)
*G06Q 30/0601* (2023.01)
*G06Q 50/04* (2012.01)

(52) U.S. Cl.
CPC ..... *G06Q 30/0621* (2013.01); *G06Q 30/0641* (2013.01); *G06Q 50/04* (2013.01)

(58) Field of Classification Search
USPC ........................................................ 705/2
See application file for complete search history.

(56) References Cited

U.S. PATENT DOCUMENTS

2018/0114285 A1\* 4/2018 Coden ..................... G06Q 50/12
2019/0221299 A1\* 7/2019 Chien ..................... A23L 33/00

\* cited by examiner

SYSTEM AND METHOD FOR DISPENSING A CUSTOMIZED NUTRACEUTICAL PRODUCT

RELATED APPLICATIONS

This patent application is continuation-in-part utility patent application that claims priority to and incorporates by reference in its entirety, the U.S. utility patent application titled "SYSTEM AND METHOD FOR DISPENSING A CUSTOMIZED NUTRACEUTICAL PRODUCT" (Ser. No. 17/108,928) that was filed on Dec. 1, 2020 and that is slated to issue as U.S. Pat. No. 11,710,551 on Jul. 25, 2023.

BACKGROUND OF THE INVENTION

The invention relates generally to systems and methods for dispensing nutraceutical products (collectively, the "system"). More specifically, the system dispenses a customized nutraceutical product that is created for consumption by a particular individual. The recipe of the nutraceutical provided to a particular individual can be selectively modified by the system based on one or more attributes of the individual ingesting nutraceutical product, as well as relevant environment factors such as time of year, temperature, sunlight, humidity, etc.

The term "nutraceuticals" covers a wide range of products that are consumed by human beings in a solid or liquid form. A nutraceutical is ingested by a human being for the purposes of obtaining a health or medical benefit. Nutraceuticals are sometimes referred to as "functional foods" such as yogurt, fresh bread, cereal bars, snack bars, frozen baked goods, various drinks, etc. or as "dietary supplements" such as vitamins, probiotics, antioxidants, fortified dairy products, botanicals, amino acids, minerals, and enzymes. In some contexts, a nutraceutical is in the form of a liquid that is sprayed into an orifice of the individual consuming the nutraceutical.

According to Stock News Magazine, the global nutraceutical market is expected to grow from $31.69 billion in 2017 to $56.52 billion in 2025. According to Grand View Research, the compound annual growth rate for the nutraceutical industry from 2016 through 2024 will be 9.6%. The growing demand and variety of nutraceutical products cannot be denied. That demand is attributed at least in part to a rising awareness of cardiovascular disorders, and the benefits that nutraceuticals can provide. Such demand may be particularly strong among working professionals with inactive lifestyles and non-optimal diets.

As written in the International Journal of Preventive Medicine in December of 2014, nutraceutical products are increasingly viewed as viable alternatives to pharmaceutical products in an effort to improve health, mitigate or even prevent chronic diseases, increase life expectancy, mitigate the negative impacts of age, and to otherwise delivery physiological benefits and therapeutic effects:

"Recent studies have shown promising results for these compounds in various complications. In the present review much effort has been devoted to present new concepts about nutraceuticals based on their diseases modifying indications. Emphasis has been made to present herbal nutraceuticals effective on hard curative disorders related to oxidative stress including allergy, alzheimer, cardiovascular, cancer, diabetes, eye, immune, inflammatory and Parkinson's diseases as well as obesity [Abstract]." Int J Prev Med 2014 December; 5(12):1487:99.

A significant obstacle in many endeavors relating to healthcare is the lack of efficacy in a one size fits all approach. The health status, requirements, and overall well-being of two individuals can be differentiated on the basis of genetics, medical history, living/work environments, diet, age, gender, race, allergies, and current medical treatments. The impact of these different factors is supported by many years of independent research, and medical science is continuously capturing experimental data and insights relating to the various factors. Despite all that investigative and analytical work, the delivery of nutraceutical products to consumers is not specifically tailored to address any of these different attributes. As such, the efficacy of nutraceutical products in the prior art are substantially and needlessly limited by a one size fits all approach.

It would be desirable for a nutraceutical dispensing system to provide users with customized nutraceutical products tailored to their individual needs, status, and other attributes that are relevant to the individual user.

Unfortunately, the prior art affirmatively teach away appears to away from the capability of providing customized nutraceutical products. The prior art addresses the problems of different consumer attributes by creating an ever increasing universe of non-customized products that are sometimes marketed on the basis of a single consumer attribute rather than creating products that are customized to address the needs of the individual consumers based on a larger or even comprehensive set of characteristics pertaining to the consumer. In particular, the prior art affirmatively teaches away from individually customized nutraceutical products that can be calibrated to work within the constraints of the delivery mechanism to achieve sublingual absorption as a single dose.

The system can be further understood as described in the Summary of the Invention section set forth below.

SUMMARY OF THE INVENTION

The invention relates generally to systems and methods for dispensing nutraceutical products (collectively, the "system"). More specifically, the system dispenses a customized nutraceutical product that is created for consumption by a particular individual. In some embodiments, the customized nutraceutical product can even if be specifically designed to address the current health of the consumer, at a particular location, and at a particular time of year. The recipe of the nutraceutical provided to a particular individual can be selectively modified by the system based on one or more attributes of the individual ingesting nutraceutical product, as well as potentially influenced relevant environment factors such as time of year, temperature, sunlight, humidity, etc.

The system provides for the creation of a customized nutraceutical that is intended to be consumed by a specific user. Customized nutraceutical products are typically human beings, but such products can also be used with a broad range of animals be they livestock on a farm, beloved family pets, or animals that fulfill very specific purposes such as race horses, rescue dogs, etc. The recipe for creating the customized nutraceutical is modified in at least one way as a result of at least one attribute relating to the intended consumer of the customized nutraceutical. In many embodiments of the system, the recipe will be selectively modified in many different ways based on the aggregate impact of numerous relevant attributes. Recipes can be modified in terms of ingredients as well as in terms of the process steps for the creation of the applicable nutraceutical. Different embodiments of the system can involve different recipe variations and different consumer attributes that selectively influence those variations.

The system can allow consumers of customized nutraceuticals to interact directly with the system or through other human representatives. Health care providers working with a particular consumer of customized nutraceuticals can also be empowered to impact the operations of the system in some embodiments of the system.

The system can transform a general purpose computer into a specialized machine that improves the efficacy of nutraceuticals by modifying the nutraceutical recipes to address relevant attributes of the consumer who will ultimately be ingesting that nutraceutical.

The system can utilize a wide variety of different information technology infrastructures and components for processing information.

The system can utilize a wide variety of different manufacturing components. In some embodiments of the system, the system also provides for the automated manufacturing of customized components. In some instances, such production can occur in a real time basis at onsite kiosks accessed by consumers and their representatives.

The system can create and dispense a nutraceutical products that are specifically tailored to individual users to be taken in single doses.

The system can be further understood in terms of the drawings described below.

BRIEF DESCRIPTION OF THE DRAWINGS

Many features and inventive aspects of the system are illustrated in the Figures which are described briefly below. However, no patent application can disclose through the use of text descriptions or graphical illustrations, all of the potential embodiments of an invention. In accordance with the provisions of the patent statutes, the principles and modes of operation of the system are explained and illustrated with respect to certain preferred embodiments. However, it must be understood that the components, configurations, and methods described above and below may be practiced otherwise than is specifically explained and illustrated without departing from its spirit or scope. Each of the various elements described in the glossary set forth in Table 1 below can be implemented in a variety of different ways while still being part of the spirit and scope of the invention.

Figures 1, 1A:
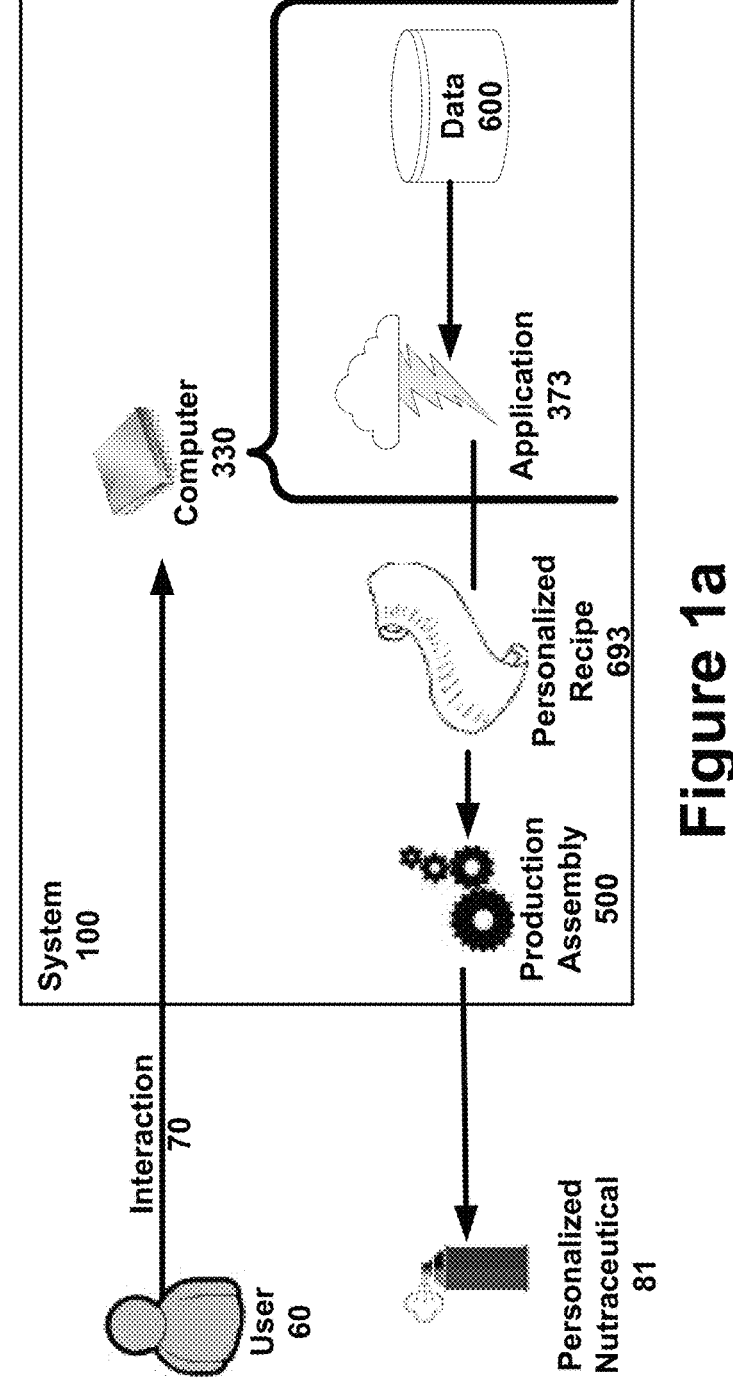
FIG. 1 is a block diagram illustrating an example of a user interacting with a system to prompt the system to create and delivery of a customized nutraceutical.
FIG. 1a is a more detailed block diagram illustrating an example of a user interacting with the system through a computer to create a personalized recipe relative to the user that is submitted to a production assembly which subsequently manufactures a personalized nutraceutical product.

The drawings described briefly above can be further understood in accordance with the Detailed Description section set forth below.

DETAILED DESCRIPTION

The invention relates generally to systems and methods for dispensing nutraceutical products (collectively, the "system"). More specifically, the system dispenses a customized nutraceutical product that is created for consumption by a particular individual. The recipe of the nutraceutical provided to a particular individual can be selectively modified by the system based on one or more attributes of the individual ingesting nutraceutical product, as well as potentially influenced relevant environment factors such as time of year, temperature, sunlight, humidity, etc.

I. Glossary of Terminology

All element numbers referenced in the text below are listed in Table 1 along with an element name and definition.

| Element Number | Element Name | Element Definition and Descriptions |
|---|---|---|
| 50 | PHYSICAL LOCATION | A geographic position in the non-virtual, physical world. In most embodiments of the system 100, data 600 is processed and communicated over a network 310 to support the manufacturing of a personalized nutraceutical 81. In describing the system 100 and in supporting claim limitations, it may be helpful to keep in the mind the following physical locations 50: (1) the physical location 50 of the user 60 when the user 60 initiates an interaction 90 with the system 100; (2) the physical location 50 of the computer 330 running the computer program 373 and housing the data 600 that includes health attributes 640 used to selectively influence the computer program 373 in modifying the recipe 692 into a personalized recipe 693; (3) the physical location 50 of the production assembly 500 that manufactures the personalized nutraceutical 81; and (4) the physical location 50 of the user 60 when the user 60 is given access to the personalized nutraceutical 81. In some embodiments, all four physical locations 50 can be the same. In many embodiments, the physical location 50 where the user 60 initiates the interaction 90 and where the user 60 receives the personalized nutraceutical 81 are identical. In still other embodiments, the user 60 interacts with the system 100 at the same location of production assembly 500, with a server 353 positioned as a second and remote physical location 50. In some embodiments of the system 100, the system 100 will monitor temperature, sunlight, humidity, and other environmental data 600 at the locations for the purposes of optimizing the value of the nutraceutical 81 to users 60. |
| 60 | USER | A user 60 is a being who either interacts directly with the system 100 or is an individual who interacts indirectly with the system 100 through an intermediary, such as a representative 64. Examples of users 60 include but are not limited to: (A) human beings who consume the personalized nutraceutical product 81 of the system 100 (i.e. consumers 62); (B) |

-continued

| Element Number | Element Name | Element Definition and Descriptions |
|---|---|---|
| | | human beings who interact directly with the system 100 on behalf of consumers 62 (i.e. representatives 64); (C) providers 66; and (D) administrators 68. Users 60 can interact with the system 100 through the IT platform 300 that can utilize a wide variety of different computers 330. |
| 62 | Consumer | A living organism who consumes the nutraceutical product 80 created by the system 100. The consumer 62 is typically a human being, but in some embodiments, the nutraceutical product 80 can be created for other types of animals or even plants. Non-human examples of consumers 62 can include livestock on farm, beloved family pets, or animals serving special purposes such as racehorses, bomb sniffing dogs, etc. Non-human consumers 62 will involve their own sets of health attributes 640, some of which will common with human consumers 62 and other information which would not. For example, the breed of a dog or horse will greatly impact their overall health assessment and the processing of the recipe computer 330 to derive the optimal personalized recipe 693. |
| 64 | Representative | A user 60 who interacts with the system 100 on behalf of someone else who actually consumes the nutraceutical product 80, i.e. a consumer 62. |
| 66 | Provider | A user 60 who is providing health care services to a consumer 62. Examples of providers 66 can include physicians, dentists, nurse practitioners, physician assistants, midwives, and other similar professionals, as well as individuals acting on behalf of such professionals. Data 600 provided by providers 66 can be particularly useful in selectively impacting the formulation for the customized nutraceutical 81. |
| 68 | Administrator | A user 60 who interacts with the system 100 in order to maintain and support the functionality of the system 100. Administrators 66 will often be personnel such as employees and contractors of the business or organization that makes the system 100 available to other users 60. |
| 70 | INTERACTION | An action or a communication occurring between the user 60 and the system 100. Interactions 70 can occur through different components of the IT platform 300 and a user 60. |
| 80 | NUTRACEUTICAL PRODUCT | A solid or liquid product that is ingested by a consumer 82 for the purpose of obtaining a medical benefit. Nutraceutical products 80 are sometimes referred to as "functional foods" (such as yogurt, fresh bread, cereal bars, snack bars, frozen baked goods, and various beverages) but are most commonly referred to as "dietary supplements" (such as vitamins, probiotics, botanicals, amino acids, minerals, and enzymes). |
| 81 | Personalized Nutraceutical/Customized Nutraceutical | A nutraceutical product 80 that is specifically created for a particular consumer 62 where the recipe 592 is selectively influenced by at least one health attribute 540 relating to the particular consumer 62. |
| 82 | Liquid Nutraceutical | A nutraceutical product 80 that exists in a liquified form. |

-continued

| Element Number | Element Name | Element Definition and Descriptions |
|---|---|---|
| 84 | Sprayed Nutraceutical | A liquid nutraceutical 82 that is sprayed into the mouth of a consumer 62. |
| 86 | Dose | A quantity of nutraceutical product 80 to be taken at a single time. |
| 88 | Powder | Fine, dry particles produced by grinding, crushing, drying, disintegration, or other similar process of a solid substance. The personalized nutraceutical 81 can be in the form of a powder 88. In many embodiments, the powder 88 will be intended to be reconstituted to a liquid before by a user 60 by the addition of water before it is consumed by the consumer 62. |
| 90 | DISPENSER/CONTAINER | A mechanism by which one or more doses of the nutraceutical product 80 is delivered to the consumer 82. In many embodiments, the dispenser 90 will hold a single dose 86 of a sprayed nutraceutical 84. |
| 92 | Single-Dose Dispenser | A dispenser 90 that holds only a single dose 86 of the nutraceutical product 80. |
| 94 | Spray Dispenser | A dispenser 90 for a sprayed nutraceutical 84. |
| 100 | SYSTEM | A collection of subsystems, assemblies, components, devices, and data 600 that can perform the function of producing a personalized nutraceutical 81 for a specific consumer 62. A system 100 includes: (A) a production device 500 to manufacture the personalized nutraceutical 81; and (B) an IT platform 300 that is enabled to control the production device 500 and selectively modify the recipe 692 into a personalized recipe 693 based on one or more health attributes 640 associated with the intended consumer 62 of the personalized nutraceutical 81. |
| 110 | Integrated System or Kiosk | An implementation of the system 100 where a single integrated assembly or device includes one of the following: (a) a production device 500; and (b) a computer 330 local to the user 60 for initiating an interaction 70 with the system 100. |
| 300 | IT PLATFORM/ IT ARCHITECTURE | A collection of two or more computers 330 connected across a network 310 that enables the functionality of the system 100. The IT platform 300 provides the means by which: (1) a user 60 can interact 90 with the system 100; (2) the software application 373 selectively modifies a recipe 692 into a personalized recipe 693, with that processed selectively influenced by one or more health attributes 640; (3) and communicate the personalized recipe 693 to the production assembly 500 for the production of a personalized nutraceutical 81 from the personalized recipe 693. |
| 310 | Network | A pathway between two computers 330 that is enabled to transmit data 600. Examples of networks 310 include but are not limited to the Internet, LANs, WANs, the World Wide Web, and other public, private, and semi-public/semi-private networks. |
| 330 | Computer | An electronic device that is used for storing and processing data 600. A computer 330 can be of various computer types 340 and be comprised of a variety of computer components 370. |

-continued

| Element Number | Element Name | Element Definition and Descriptions |
|---|---|---|
| 340 | Computer Types | A computer 330 can be categorized in numerous ways that are not related to the components 370 making up the computer 220 |
| 341 | General Purpose Computer | A computer 330 that allows the user 60 to freely add or remove programs 373 from the computer. Common examples of general purpose computers include desktop computers, laptop computers, tablet computers 345, and smart phones 347. |
| 342 | Embedded Computer | A computer 330 that is embedded in a device, such as a production assembly 500. Industrial equipment such as the production assembly 400 may utilize one or more embedded computers 342 to control the operations of the manufacturing process. |
| 343 | Stationary Computer | A computer 330 such as a desktop computer or a laptop computer that is not readily usable as the user walks or otherwise moves around. |
| 344 | Mobile Computer | A computer 330 that is easily moved as the user moves. Wearable computer 346 are mobile computers 344, as are tablet computer 345 and smart phones 347. |
| 345 | Tablet Computer | A mobile computer 344 that is in the form of a tablet. |
| 346 | Wearable Computer | A mobile computer 344 that is worn by the user 60. |
| 347 | Smart Phone | A mobile computer 344 that is in the form a smart phone. |
| 348 | Watch Computer | A wearable computer 346 that is worn on the wrist like a wristwatch. |
| 350 | Local Computer/Client Device | A computer 330 that is located either at the physical location 50 of the user 60 or the physical location 50 of the production assembly 500. |
| 352 | Remote Computer/Server | A computer 330 that is remote from the physical location 50 of the user 60 and the physical location 50 of production assembly 500. |
| 370 | Computer Components | A computer 330 is comprised of a variety of components, such as an interface 371, a processor 372, a program 373, a storage component 374, a database 375, and a communications component 376. |
| 371 | Interface | Means by which a user 60 and a computer 330 interact, typically through a graphical user interface that consists of screens, buttons |
| 372 | Processor | A central processing unit (CPU) that performs the instructions set forth in the program 373. |
| 373 | Program or Application | A collection of instructions that are submitted to the processor 372 enabling the computer 330 to perform certain functions. The application(s) 373 or program(s) 373 can implement a variety of heuristics and/or algorithms so that the resulting recipe for a customized nutraceutical 81 is selectively influenced by even subtle combinations of factors that exceed 1,000,000 variables. In some embodiments, the application 373 is enhanced over time from feedback and/or a machine learning component. |
| 374 | Storage Component | A mechanism by which data 600 is stored such that in can be accessed by the computer 330 after the computer is turned off and then on again. |

-continued

| Element Number | Element Name | Element Definition and Descriptions |
|---|---|---|
| 375 | Database | A specialized program 373 that stores and organizes a structured set of data 600 that is stored on the storage component 374 in a manner such that other computer programs 373 can add, update, delete, and read information. |
| 376 | Communication Component | A part or device that allows a computer 330 to connect to a network 310. The communication component 376 is also commonly referred to as an adaptor. |
| 380 | Peripheral Devices | Devices that interact or interface with a computer 330. |
| 382 | Input Devices | A peripheral device 380 that can be used to input data 600 to the system 100. In this context, the frame of reference for the word "input" is the computer 330 receiving the data 600. |
| 383 | Sensor | An input device 382 that captures, readings, measurements, or other forms of information. |
| 384 | Camera | A sensor 383 that captures sensor readings in the form of images. |
| 385 | Microphone | A sensor 383 that captures audio information. |
| 386 | Retina Scanner | A type of camera 384 that captures information relating to the retina of a user 60 such that the user 60 can be identified using the information. |
| 387 | Keyboard | A panel of keys that can be used to submit information to a computer 330. Keyboards can be physical or electronic. |
| 390 | Output Devices | Devices that communicate information to the user 62. In this context, the frame of reference for the word "output" is the computer 330 displaying or playing data 600. |
| 391 | Screen | An output device 390 that displays visual information. |
| 392 | Speaker | An output device 390 that plays audio information. |
| 500 | PRODUCTION ASSEMBLY/ PRODUCTION PLATFORM | A device, assembly, or other configuration of components that enable the manufacture of nutraceutical product 80. The production assembly 500 can include but are not limited to: storage containers 510 for storing ingredients 520, mixing containers 520, heating elements 540, stirring elements 550, cooling elements 560, controls 570, and computers 330. |
| 510 | Storage Container | An object that is used by the production device 500 to store a solid, liquid, or gas. |
| 520 | Ingredient | A solid, liquid, or gas that is stored in a storage container 510 and available for use in making nutraceutical products 80. |
| 530 | Mixing Container | A vessel used to hold ingredients 520 as they are mixed in making nutraceutical products 80. |
| 540 | Heating Element | A device used to apply heat in the making of nutraceutical products 80. |
| 550 | Stirring Element | A device used to mix ingredients 520 in a mixing container 530. |
| 560 | Cooling Element | A device used to remove heat in the making of nutraceutical products 80. |
| 570 | Control | A switch, button, knob, dial, or some other similar mechanism that impacts the operation of the production device 500. |
| 600 | DATA | Information that is accessible to the system 100, created by the system 100 or otherwise subject to the processing of the system 100. The system 100 can store, create, update, and delete data 600 through the IT Platform 300 used by the system 100. Data 600 includes both |

-continued

| Element Number | Element Name | Element Definition and Descriptions |
| --- | --- | --- |
| | | inputs 610 and outputs 690. Data 600 can originate from a variety of different data sources 680. The singular form of "data" is "datum". |
| 610 | Inputs | An input 610 is data 600 utilized by the system 100 in creating an output 590. In this context, the frame of reference for the term "input" is that the of software application 373. |
| 620 | User Profile | A user profile 620 is a collection of data 600 stored on the database 375 that relates to the user 60. A user profile 620 can include all data 600 relating to the health attributes 640 of the user 60. A user profile 620 is linked to a particular user 60 through an ID 622 and password 624. A user profile 620 pertains to a particular consumer 62. |
| 622 | ID | A key or other unique identifier on the system 100 that is associated with the applicable user profile 620. |
| 624 | Password | A secret word, phrase, string of characters, or biometric identifier associated with a user 60 that allowed the user 60 to access the system 100 as the particular user 60. |
| 640 | Health Attributes | A health attribute 640 is a datum 600 pertaining to the consumer 62 that can be used to selectively influence recipe 592 and/or composition 594 of the personalized nutraceutical 81 created for that consumer 62. Examples of health attributes 640 can include but are not limited to age 642, weight 644, gender 646, race 648, profession 650, location 652, medical history 654, current medical status 656, current prescriptions 658, current treatments 660, self-assessments 662, health metrics 664, and virtually any other attribute relating to the consumer 62. |
| 642 | Age or Chronological Age | The length of time that the consumer 62 has lived. |
| 643 | Biological Age or Advanced Health Metric | A derived health attribute that is calculated by the application(s) 373 of the system 100. The system 100 can calculate a metric to assess biologically rather than chronologically how old the consumer 62 is. By way of example, a human being who is only thirty years of age may possess health attributes such as blood pressure, cholesterol, etc. that are common for someone twice their age. The system 100 can dynamically assess biological age 643 based on the specific outcomes desired by the consumer 62. |
| 644 | Weight/Mass | The quantity of matter comprising the consumer 62. |
| 646 | Gender | The state of being male, female, or other genders. |
| 648 | Race | A category of humankind that shares certain distinctive physical traits to which the consumer 62 belongs. |
| 650 | Profession/Job | An occupation held by the consumer 62. |
| 652 | Location | A geographic position associated with the consumer 62. A location 652 can be a residential location 652 or a work location 652. |
| 654 | Medical History | A collection of data 600 relating to the past healthcare status and treatments of the consumer 62. |
| 655 | Family Medical History | A collection of data 600 relating to the medical history of the consumer's family. |
| 656 | Current Medical Status | A collection of data 600 relating to the consumer's health condition. |

-continued

| Element Number | Element Name | Element Definition and Descriptions |
|---|---|---|
| 658 | Current Prescriptions | A collection of data 600 relating to the pharmaceutical products utilized by the consumer 62. |
| 660 | Current Treatments | A collection of data 600 relating to ongoing medical procedures and care received by the consumer 62. |
| 662 | Self-Assessments | An assessment by a consumer 62 that is submitted to the system 100 relating to the perceived health of the consumer 62. Assessments can relate to happiness/unhappiness, contentment, stress, quality of sleep, quantity of sleep, energy levels, |
| 664 | Health Metrics | Any indirect or direct health metric 664 that is not already expressly listed as an example of a health attribute 640. Examples of health metrics 664 include blood pressure, cholesterol levels, heart rate, blood cell counts, |
| 666 | Time of Year | A portion of the calendar year. The time of year 666 can be associated with certain temperatures, humidity, physical ailments, allergies, etc. that can be factored into the processing of the application 373 in defining the personalized recipe 693. |
| 668 | UV Light Metric | A health-related measurement of the consumer 62 that is captured using ultraviolet light. |
| 680 | Data Sources | A source of data 600 that is stored or utilized by the system 100. Data sources 680 can include but are not limited to sensor measurements 682, user inputs 684, previously stored data 686, and third-party sources. |
| 682 | Sensor Measurement | A datum 600 that originated as a measurement or reading captured by a sensor 383. |
| 684 | User Input | A datum 600 that originated as information inputted into the system 100 by a user 60. |
| 686 | Previously Stored Data | A datum 600 that is stored on the system 100 and used an input 610 for subsequent outputs 690. |
| 688 | Third Party Sources | A datum 600 that resides on a computer 330 outside the scope of the system 100, but accessible through a network 310 such as the Internet. By way of example, as medical information is learned and made accessible to the public, the system 100 can use such information to selectively influence the creation of personalized nutraceuticals 81. |
| 690 | Outputs | A result or output of a computer program 373 that is selectively influenced by one or more inputs 610. Outputs 690 can be selectively influenced by any combination of one or more inputs 690. The frame of reference for the term "output" in this instance relates to the application 373 that outputs the personalized recipe 693. |
| 692 | Recipe/Process for making | A sequential set of process steps coupled with the necessary ingredients 520 to create a personalized nutraceutical 81. The recipe 692 can be selectively influenced by one or more inputs 610 in accordance with the computer program 373 operating the manufacturing device 400. |
| 693 | Personalized Recipe | A recipe 692 that has been selectively modified by the application 373 in accordance with one or more health attributes 640. |

| Element Number | Element Name | Element Definition and Descriptions |
|---|---|---|
| 694 | Composition | A technical description of a nutraceutical product 80, with the description typically including the various components making up the nutraceutical product 80 and their various quantities. |
| 696 | Composition ID | A unique identifier for a particular personalized nutraceutical 81. The Composition ID can be series of alphanumeric characters. In some embodiments, a consumer 62 who is knows the composition ID 696 for their specific personalized nutraceutical 81 can go to a production assembly 500 and order the desired personalized nutraceutical 81 without providing information about the consumer 62 or their profile 620. |
| 697 | Recipe ID | A unique identifier for a particular personalized recipe 693. The Recipe ID can be series of alphanumeric characters. In some embodiments, a consumer 62 who is knows the composition recipe ID 697 for their specific personalized nutraceutical 81 can go do a production assembly 500 and order the desired personalized nutraceutical 81 without providing information about the consumer 62 or their profile 620. The system 100 can be implemented with more than 1 million potential variations of a template recipe 692. |
| 698 | History | All of the data 600 used by the system 100 can be potentially be stored as history for future reference by system 100 as inputs 610. |

II. Overview

Each and every individual consumer 62 has different needs in terms of nutraceuticals 80. Differences between consumers 82 are grounded in differences of health attributes 640, such as chronological age 642, biological age 643, weight/mass 644, gender 646, race 648, profession/job 650, location 652, medical history 654, family medical history 655, current medical status 656, current prescriptions 658, current treatments 660, self-assessments 662, health metrics 664, time of year 666, UV light metric 668, and other potential attributes that different consumers 62 of nutraceuticals 80.

The efficacy of nutraceutical products 80 with respect to consumers 62 in the prior art is impeded by the one size fits all approach. Implementation of the system 100 transforms a computer 300 into a highly effective machine for creating a personalized recipe 693 for the creation of a personalized nutraceutical 81 that will be more effective for the specific consumer 62 because such a personalized recipe 693 was created to address the specific attributes of that specific consumer 62.

Prior art examples of giving individualized nutraceuticals in the prior art have always involved aggregating individual vitamins in an approximation of their individual requirements such as a multivitamin tablet, a vitamin D tablet, and a magnesium tablet. This prior art process of aggregation inherently limits what can be provided to consumers 62 as individual tablets with exact combination of ingredients cannot be made. The system 100 can be implemented with far more flexibility to selectively modify a recipe 692 into a modified recipe 693 to create a personalized nutraceutical 81 rather than the template unmodified nutraceutical 80. By way of example, the system 100 can include an application 373 that creates a modified recipe from a potentially wide range inputs 610 to automatically calculate optimum nutrition requirements for each individual consumer 62 and the production capabilities to produce a liquid vitamin spray 84 that will provide the individuals consumers 62 with their personalized vitamin and mineral requirements on a monthly basis.

Prior art systems find such true customization to be too expensive and time consuming. They claim to offer personalized vitamin products, but they either offer modest predefined alternative offerings or suggested aggregate combinations of products to achieve the customized result.

To overcome this problem in the prior art, the system 100 can be implemented to provide personalized nutraceuticals 81 that are in a liquid form 82 that are sprayed 84 into the mouth of the consumer 82. The system 100 can manufacture a personalized nutraceutical 81 in the form of a liquid spray 84 that has been formulated in terms of ingredients 520 and process for making the personalized nutraceutical 81 by the algorithms embodied in the application 373. The algorithms can consist of numerous stages with up to 1,024,000 variables. After processing the finalized formula 693 will be sent to the manufacturing assembly 500 where it can be made into a single liquid vial for administration as a fine oral spray via the oral mucosa. This formulation can change throughout the year dependent on need and will be supplied with modifications on a monthly basis thus covering the nutritional requirements of the individual for the year.

The system 100 does not need to calibrate the delivery mechanism for a customized nutraceutical 81, but it can be calibrated to work within the operating parameters of the delivery mechanism. This can be done in order to achieve sublingual absorption (absorption through blood vessels under the togue rather than the digestive track), which has advantages of speed and efficiency relative to digestive absorption. A single dose of a such a nutraceutical 81 will typically have a single dose of not more than 3-5 sprays. Too many sprays, and "pooling" at the bottom of the mouth would result in swallowing, which defeats the aims of sublingual absorption. Too few sprays, and insufficient nutraceutical 81 is delivered to the user 60. A typical spray may vary between 2 mg to 3 mg of nutraceutical 81. In some embodiments, a practical limit of 4 2.5 mg sprays is implemented in a "bespoke" quantity of vitamins and supplements.

The system 100 can formulate a recipe 692 for a customized nutraceutical 81 which achieves the correct level of vitamins, probiotics, antioxidants, fortified dairy products, botanicals, amino acids, minerals, and enzymes etc. for achieving sublingual absorption. This can be done will influencing taste, stability, and other factors as well. Simply combining liquids into a spray bottle and spraying will not achieve the desire absorption.

III. Introduction of Elements

FIG. 1 is a block diagram illustrating a user 60 prompting the system 100 to provide the user 60 with a personalized nutraceutical 81. The customized nutraceutical 81 can be created using a recipe 692 that is modified into a personalized recipe 693 by the application 373. The modification of the recipe 692 is done selectively, in accordance with at least one attribute 640 of the intended consumer 62 of the customized nutraceutical 81. Different embodiments of the system 100 can be implemented to "factor in" different numbers of types of data 600 that will selectively influence the formulation of the customized recipe 693. The application 373 can use a variety of different algorithms and heuristics to "factor in" the various inputs. In some embodiments of the system 100, the application 373 can access a machine learning component to assist the system 100 in determining FIG. 1a is a more detailed block diagram illustrating an example of a user 62 initiating an interaction 70 with the computer 330 that is a component of the system 100. The computer 330 runs an application 373 that accesses data 600, which includes health attributes 640 of the consumer 62 to a create a personalized recipe 692 which is then sent to the production assembly 500 for the production of the personalized nutraceutical 81. In many embodiments of the system 100, there will be a feedback loop from the personalized nutraceuticals 81 produced by the system 100 and the users 60 who consume them, to the future processing of the application 373 in generating future recipes 692 for future production by future production assemblies 500.

Figure 1B:
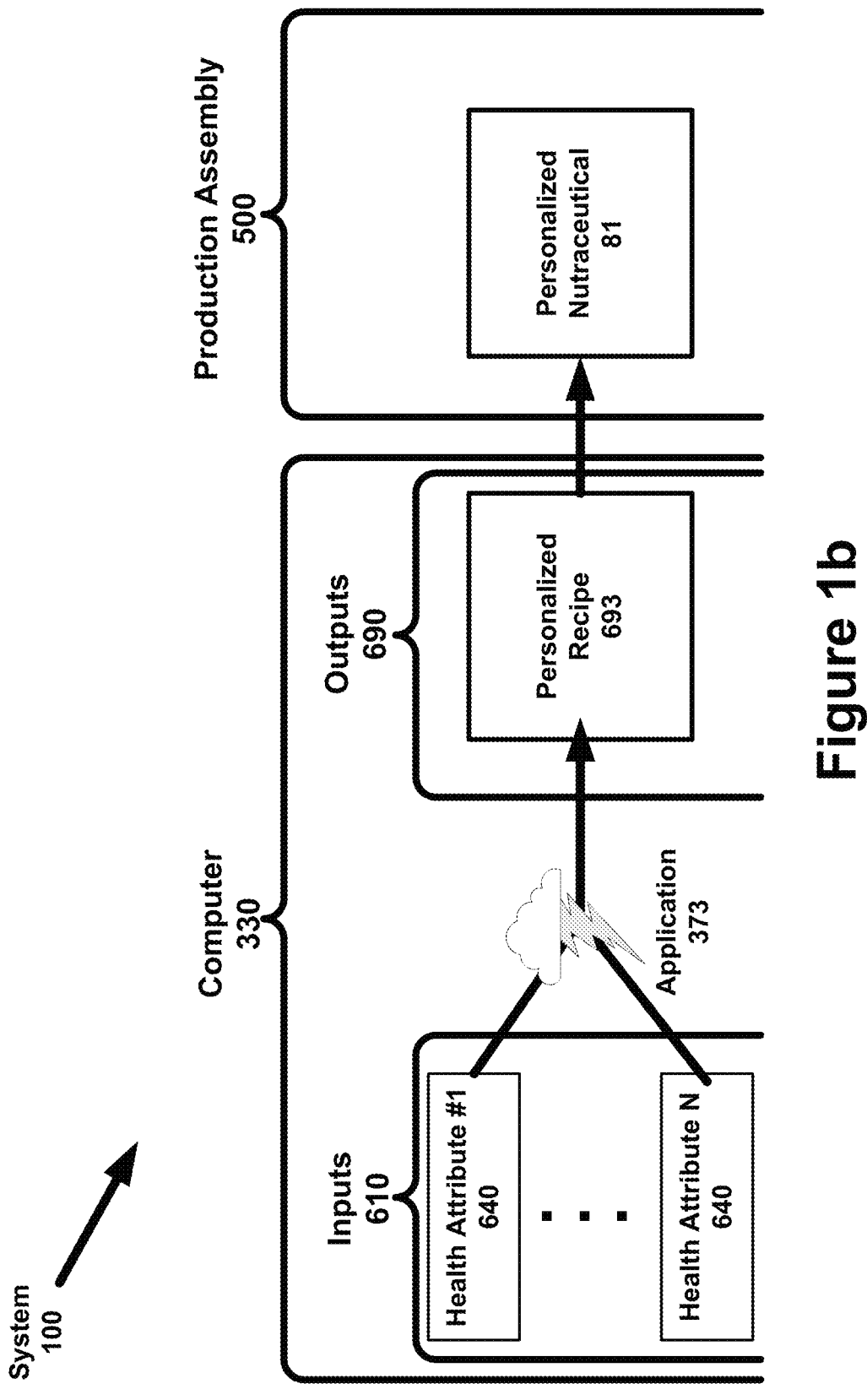
FIG. 1b is block diagram illustrating an example of different health attributes which can be inputted to the application to selectively influence a personalized recipe specified as an output of the application.

FIG. 1b is block diagram illustrating an example of different health attributes 640 which can be inputted to the application to selectively influence a personalized recipe 81 specified as an output 690 of the application 373. The outputs 690 of the application 610 are created using the inputs 610. Health attributes 640 such as age 642, weigh/mass 644, gender 646, race 648, profession/job 650, location 652, medical history 654, family medical history 655, current medical status 656, current prescriptions 658, current treatments 660, self-assessments 662, health metrics 664, time of year 66, and UV light metrics 668, and potentially other health attributes 640 can be common examples of inputs 610 that can selectively influence the outputs 690 of the application 373 through the algorithm(s) implemented by the application 373.

Figure 1C:
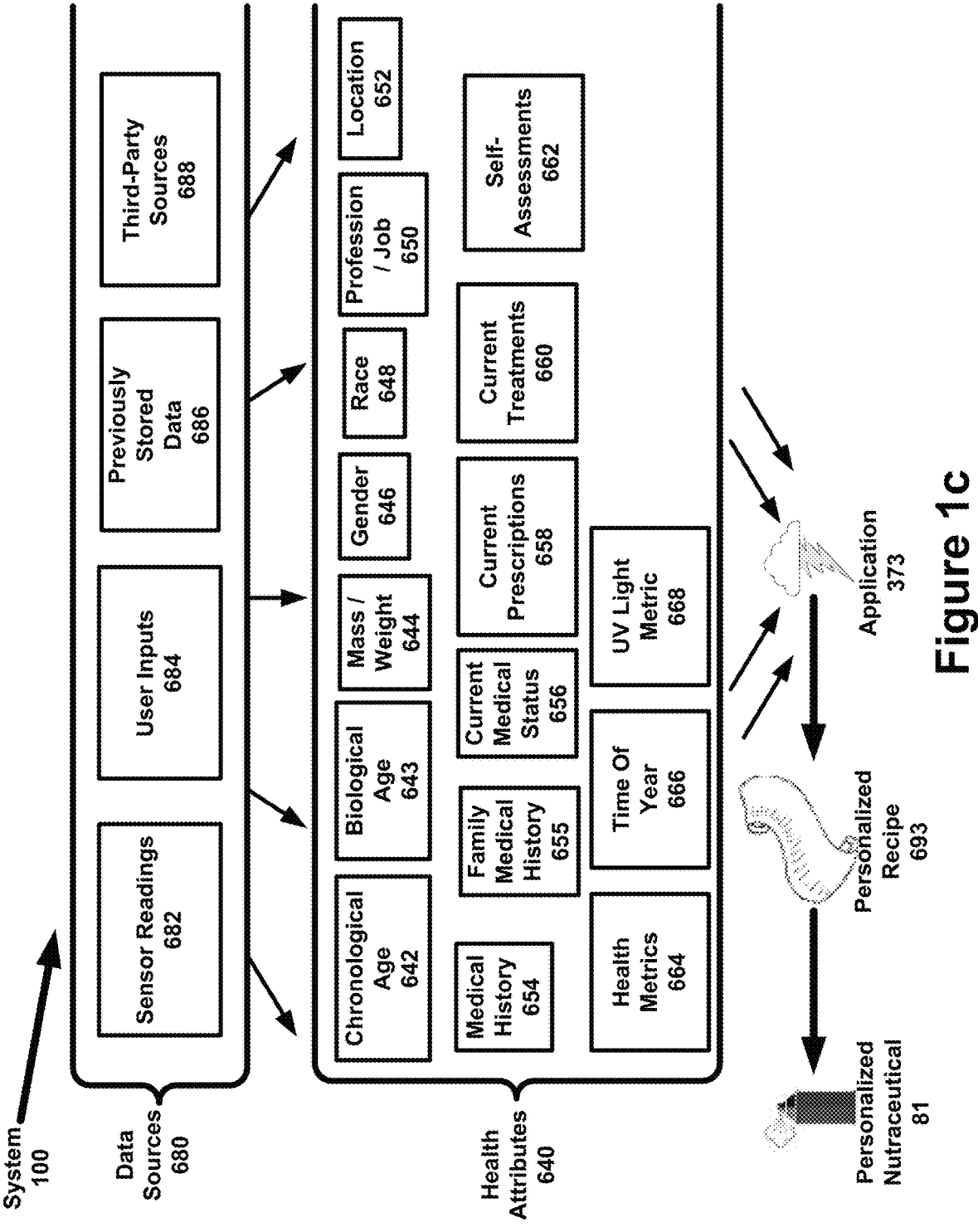
FIG. 1c is a block diagram illustrating an example of different data sources and health attributes which can collectively influence the personalized recipe that is specified by the application for creation by the manufacturing assembly of a personalized nutraceutical.

FIG. 1c is a block diagram illustrating an example of different data sources 680 and health attributes 640 which can collectively influence the personalized recipe 693 that is specified by the application 373 for creation by the manufacturing assembly 500 of a personalized nutraceutical 81.

Examples of potential data sources 680 can include sensor readings 682, user inputs 684, previously stored data 686, and third-party sources 688. Data sources 680 provide sources of data 600 that can be used as inputs 610 for the application 373 that formulates the personalized recipe 693 for the manufacturing assembly 500.

Figure 1D:
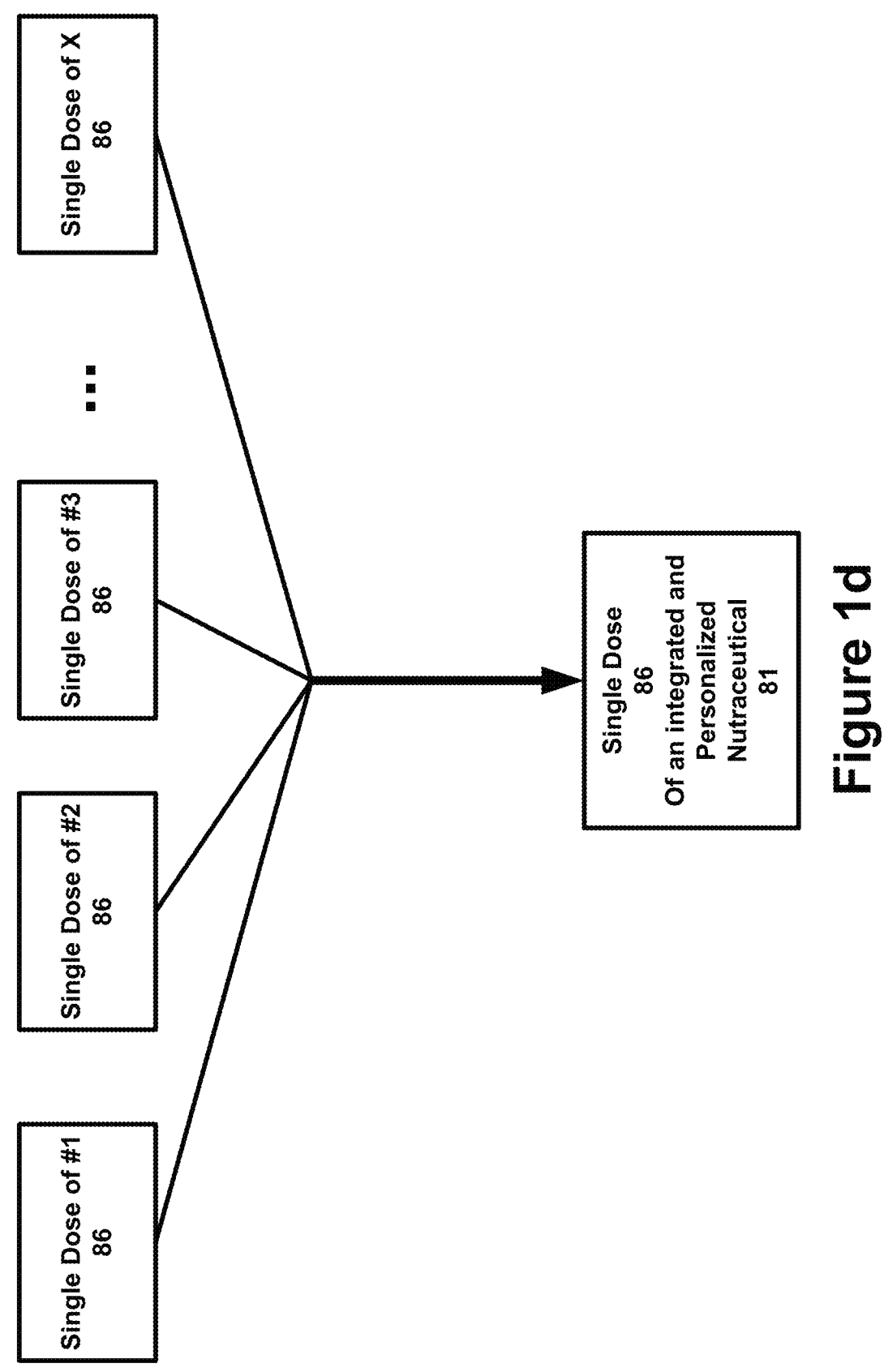
FIG. 1d is an input-output diagram illustrating an example of ingredients being combined into a single dose customized nutraceutical.

FIG. 1d is input/output diagram illustrating the different ingredients (ingredients 1, 2, 3, . . . X) being used to create a single dose 86 of a personalized nutraceutical 81. The system 100 can be implemented to provide personalized nutraceuticals 81 that are in a liquid form 82 that are sprayed 84 into the mouth of the consumer 82. The system 100 can manufacture a personalized nutraceutical 81 in the form of a liquid spray 84 that has been formulated in terms of ingredients 520 and process for making the personalized nutraceutical 81 by the algorithms embodied in the application 373. The algorithms can consist of numerous stages with up to 1,024,000 variables. It is anticipated that in the future, even a greater number of variables and possible configurations and parameters will be able to be "factored in" to the formulation of personalized nutraceuticals 81.

The system 100 does not need to calibrate the delivery mechanism for a customized nutraceutical 81 (although the system 100 could be implemented to factor in such a calibration in future advancements of delivery mechanisms) but it can be calibrated to work within the operating parameters of the delivery mechanism. This can be done in order to achieve sublingual absorption (absorption through blood vessels under the togue rather than the digestive track), which has advantages of speed and efficiency relative to digestive absorption. In some embodiments, a practical limit of 4 2.5 mg sprays is implemented in a "bespoke" quantity of vitamins and supplements.

The system 100 can formulate a personalized recipe 693 for a customized nutraceutical 81 which achieves the correct level of vitamins, probiotics, antioxidants, fortified dairy products, botanicals, amino acids, minerals, and enzymes etc. for achieving sublingual absorption. This can be done will influencing taste, stability, and other factors as well. Simply combining liquids into a spray bottle and spraying will not achieve the desire absorption.

Figure 1E:
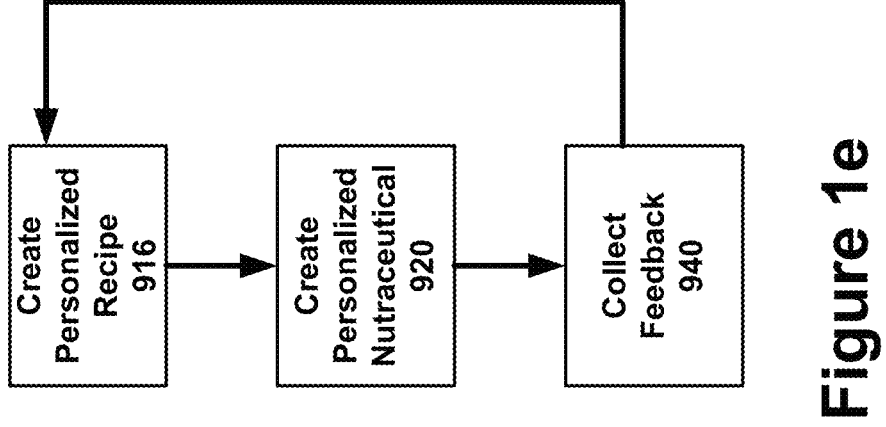
FIG. 1e is a process flow diagram illustrating an example of how the processing of the system can be continuously improved through the updating of the application (including all algorithms and heuristics) as a result of collected pertaining to past results. The system can include a perpetual feedback loop between past nutraceuticals, feedback collected from those nutraceuticals, and the applications/algorithms/heuristics used to create the recipes for future nutraceuticals.

FIG. 1e is a flow chart diagram that illustrates an example of a feedback loop that is continuously applied to improve the customization/personalization processing performed by the system 100. Such a feedback loop can include machine learning technologies if desired.

At 916, a personalized recipe is created. At 918, that recipe is used to produce the customized nutraceutical 81. At 940, feedback is collected. Feedback can be collected in the form of user behavior, user communications, and objective measures of the resulting customized nutraceutical 81. This feedback loop can be continuous throughout the use of the system 100.

IV. IT Architectures

The system 100 can be implemented using a wide variety of different architectures.

A. Example #1—Different Computers

The system 100 can be implemented in such a manner that a first computer 330 is used by the user 60 is different from a second computer 330 (such as a server) that houses the data 600 and the application 373 used to formulate the personalized recipe 692. A third computer 330 receives the personalized recipe 692 from the server 352 and uses it to manufacture the personalized nutraceutical 81 that is then delivered to the user 60.

Figure 2A:
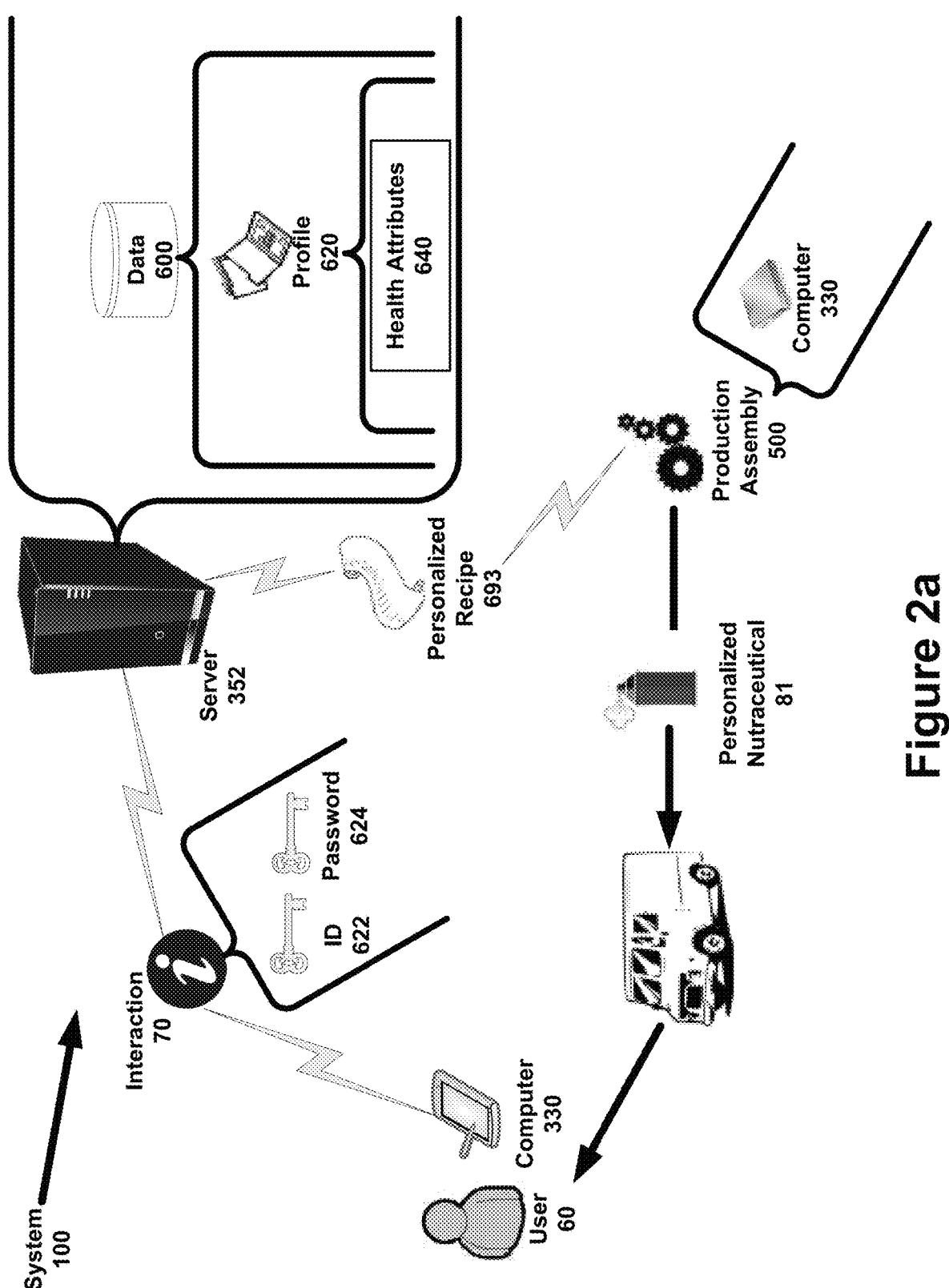
FIG. 2a is block diagram illustrating an example an information technology configuration used to implement the system where the user accesses a personal computer under their control to interact with a server managed by the business operating the system to access a profile of attributes pertaining to the user in the creation of a personalized recipe that is transmitted to a production assembly so that the personalized recipe can be used manufacture a personalized nutraceutical that is then delivered to the user.

FIG. 2*a* is block diagram illustrating an example an information technology 300 configuration used to implement the system 100 where the user 60 accesses a personal computer 330 under their control to interact with a server 352 managed by the business operating the system 100 to access a profile 620 of attributes 640 pertaining to the user 60 in the creation of a personalized recipe 693 that is transmitted to a production assembly so that the personalized recipe 693 can be used manufacture a personalized nutraceutical 81 that is then delivered to the user 60.

B. Example #2—Kiosk Combining User Interface and Manufacturing

The system 100 can be implemented as a kiosk 110 that houses one or more computers 330 for receiving interactions 70 from users as well as receiving personalized recipes 693 for the manufacture of the personalized nutraceuticals 81 from the personalized recipes 693. The kiosk 110 in this drawing integrates the production assembly 500 with the computer 330 used to receive user 60 orders.

Figure 2B:
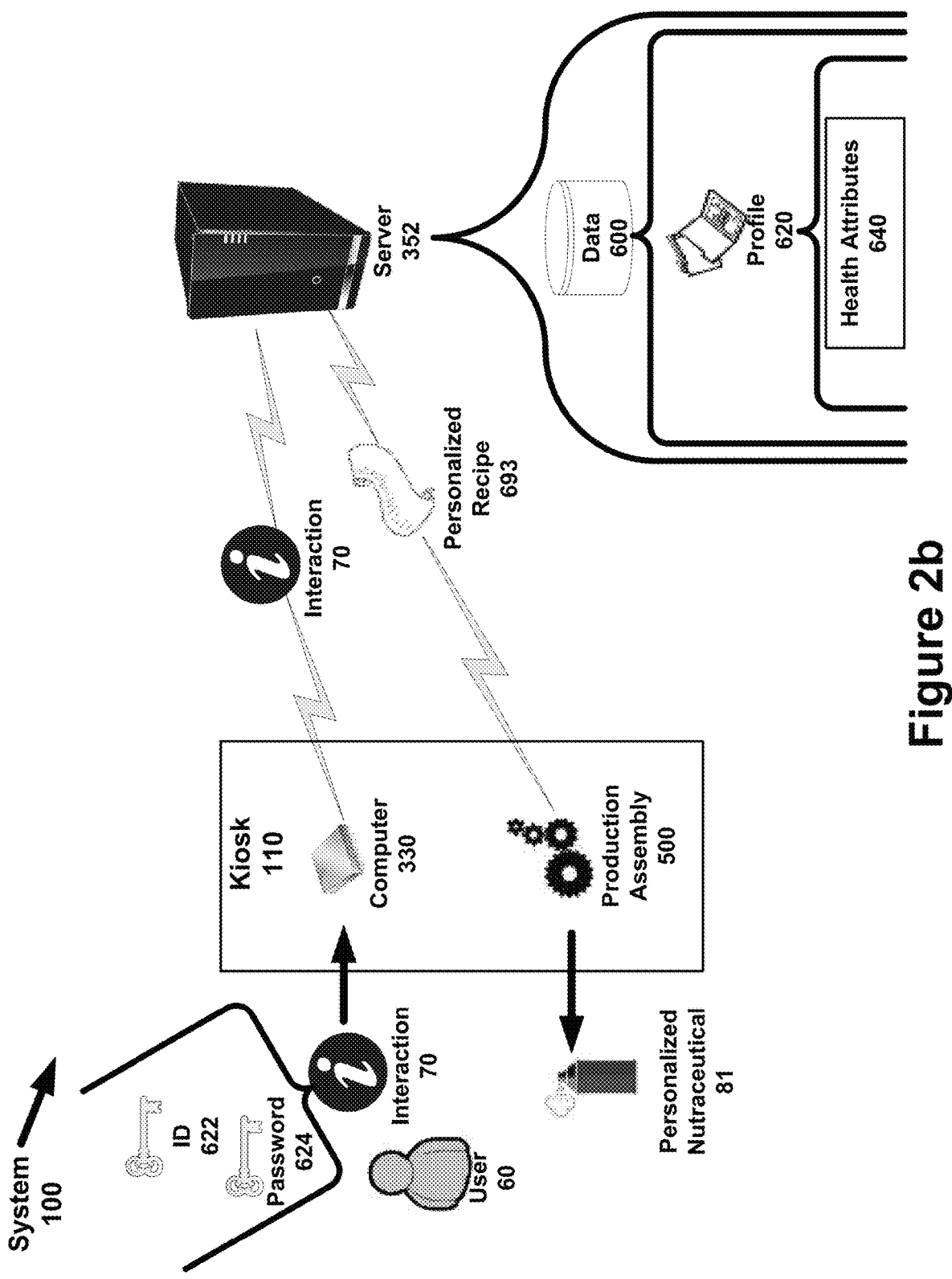
FIG. 2b is a block diagram illustrating an example of the system similar to the example of FIG. 2a, except that the computer used by the user is part of a kiosk that includes the manufacturing assembly to actually manufacture the personalized nutraceutical.

FIG. 2*b* is a block diagram illustrating an example of the system 100 similar to the example of FIG. 2*a*, except that the computer 330 used by the user 60 is part of a kiosk 110 that includes the manufacturing assembly 500 to actually manufacture the personalized nutraceutical 81 in response to the interactions 70 provided by the user 60. As illustrated in the drawing, the interactions 70 can be comprised of an ID 622 and password 624 that relates to data 600 pertaining to the user 60 that is stored on the server 352.

C. Example #3—Kiosk Using Mobile Computer for User Interface

The system 100 can be implemented such that the kiosk 110 that is local to the user 60 houses the production assembly 500 but the user 60 initiates the interaction 70 with a mobile computer 330 such as a smart phone.

Figure 2C:
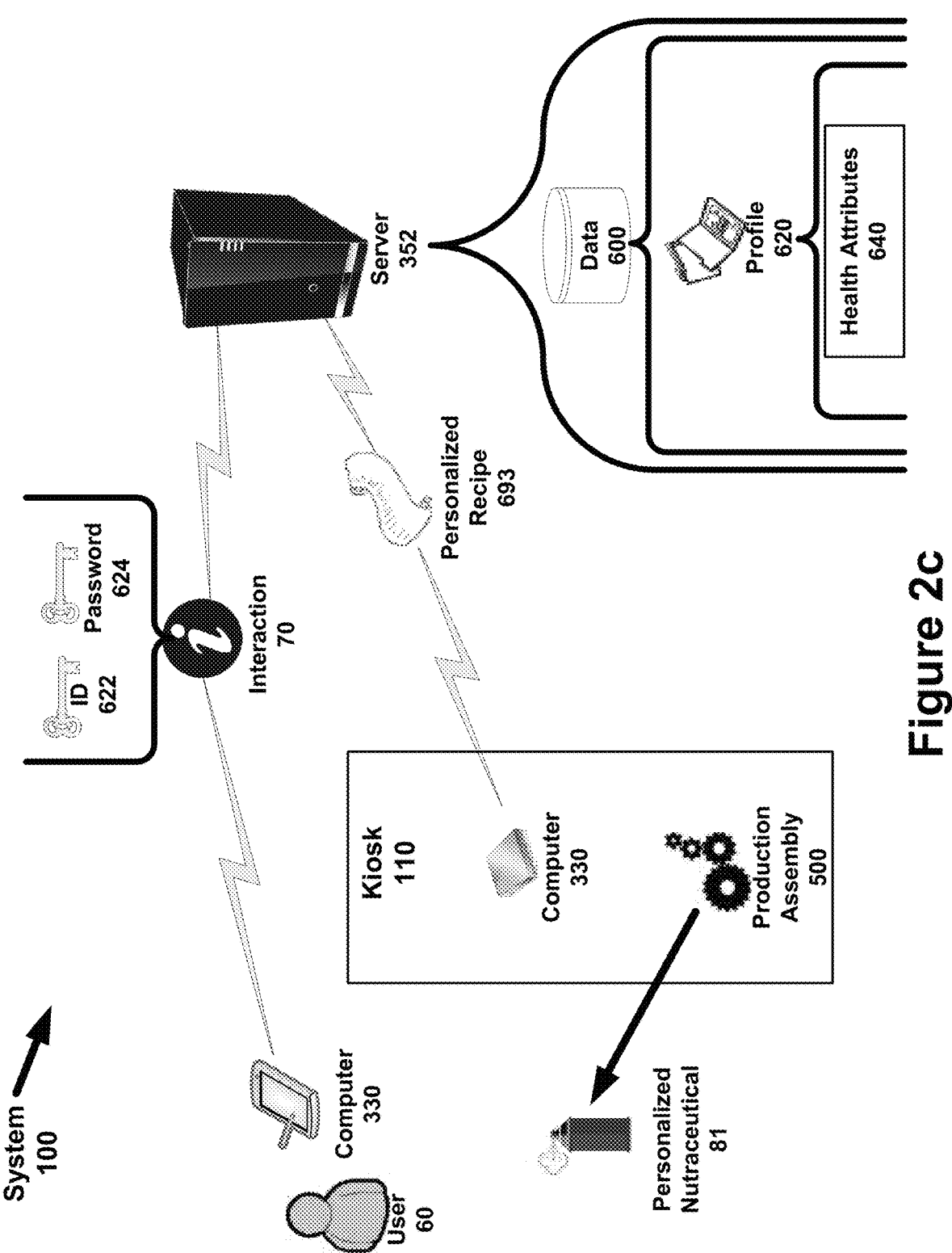
FIG. 2c is a block diagram illustrating an example of the system similar to the example of FIG. 2b except that the kiosk is not used by the user to initiate the transaction with the system.

FIG. 2*c* is a block diagram illustrating an example of the system 100 similar to the example of FIG. 2*b* except that the kiosk 110 is not used by the user 60 to initiate the transaction with the system 100.

D. Example #4—Use of Personalized Recipe ID

The system 100 can associate a recipe ID 697 with each personalized recipe 693. This can be helpful because such an approach allows the user 60 to order personalized nutraceuticals 81 without having to invoke the algorithms in the application 373.

Figure 2D:
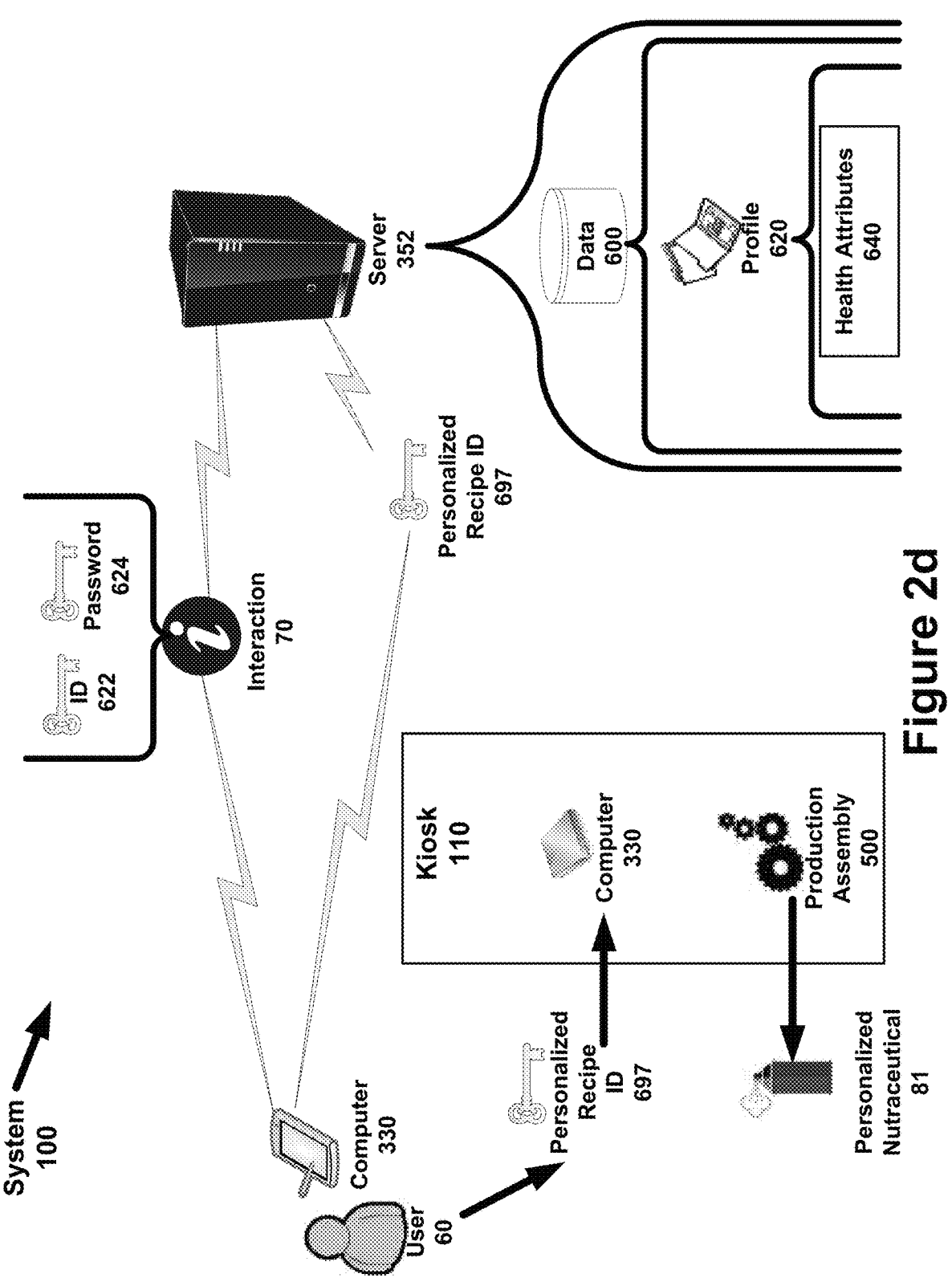
FIG. 2d is a block diagram illustrating an example of the system similar to the example of FIG. 2c except that in addition to the personalized nutraceutical, the user receives a personalized recipe ID to facilitate future interactions with the system or to otherwise make future purchases.

FIG. 2*d* is a block diagram illustrating an example of the system 100 similar to the example of FIG. 2*c* except that in addition to the personalized nutraceutical 81, the user 60 receives a personalized recipe ID 697 to facilitate future interactions 70 with the system 100 or to otherwise make future purchases.

V. Description of Components, Personnel, and Products

Figure 3A:
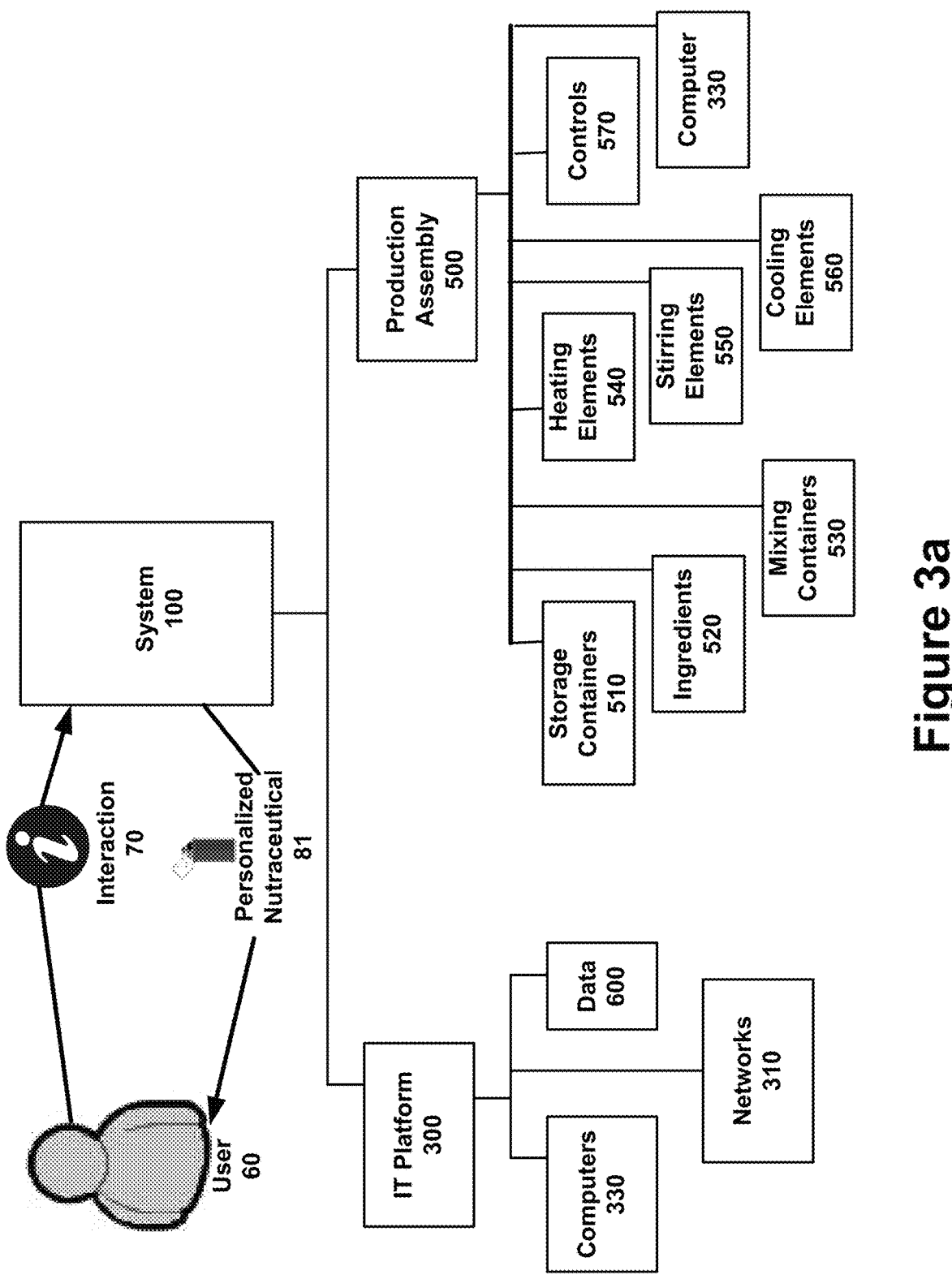
FIG. 3a is a hierarchy diagram illustrating an example of different components that can be included in the IT platform as well as the production assembly.

FIG. 3*a* is a hierarchy diagram illustrating an example of different components that can be included in the IT platform 300 as well as the production assembly 500, both of which are used by the system 100 to produce a personalized nutraceutical 81 in response to an interaction 70 initiated by the user 60. As discussed and described above, an IT platform 300 can include computers 330 (and their components), data 600 (such as inputs 610 and outputs 690), and networks 310 that connect the computers 330 together.

A. Production Assembly

A production assembly 500 can be implemented in a wide variety of different ways in terms of scale and location. The production assembly 500 can be implemented in a conventional manufacturing environment where the personalized nutraceutical products 81 are manufactured to be shipped to consumers 62. In other embodiments, the production assembly 500 can be implemented in a kiosk 110 that is local to a user 60.

A production assembly 500 can include storage containers 510 for holding ingredients 520, ingredients for producing personalized nutraceuticals 81, mixing containers 530, heating elements 540, stirring elements 550, cooling elements 560, controls 570, and computers 330.

B. Users

Figures 3B, 3C:
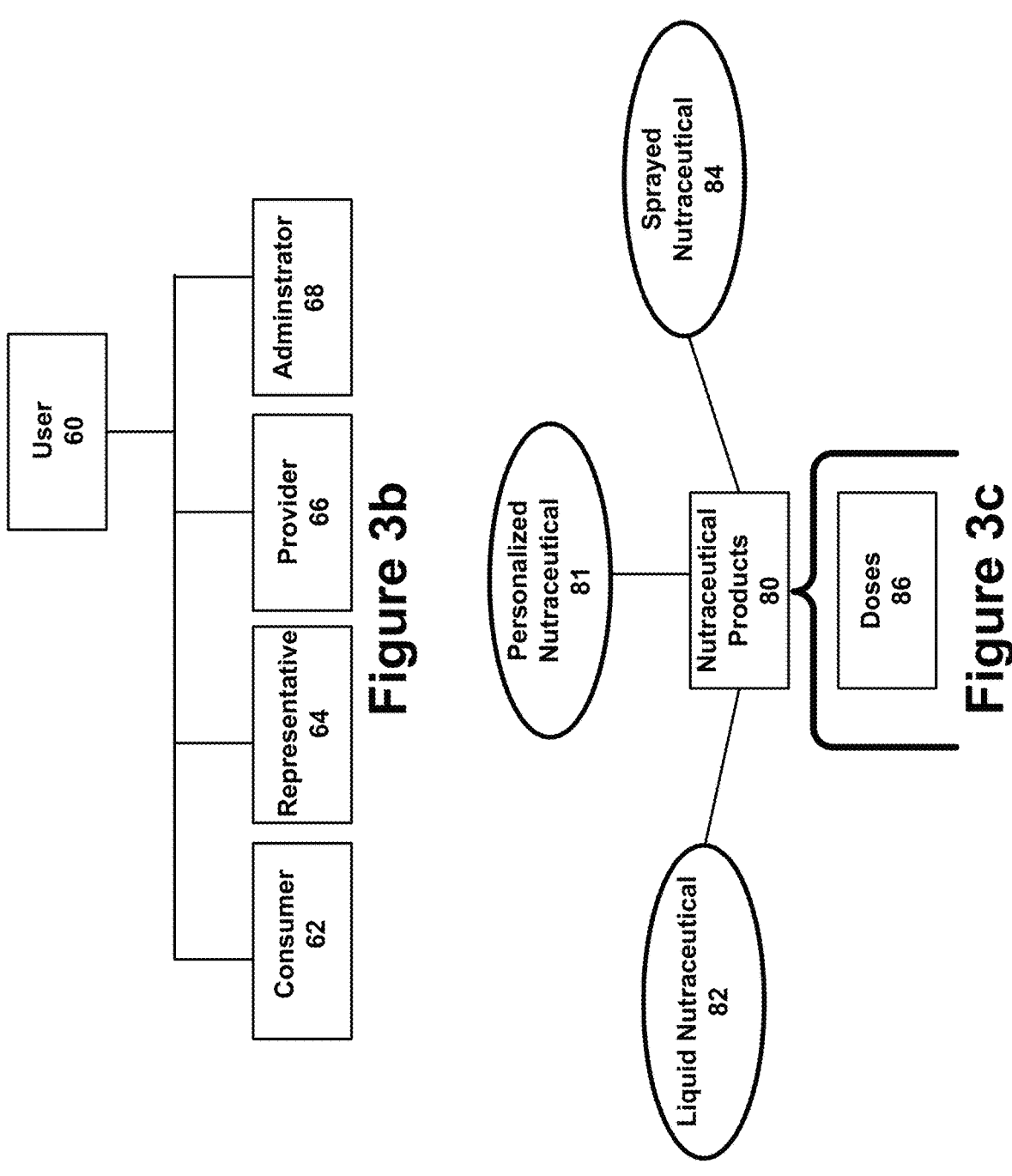
FIG. 3b is hierarchy diagram illustrating the different categories of users who can interact with the system.
FIG. 3c is a block diagram illustrating different examples of nutraceutical products and their doses.

FIG. 3*b* is hierarchy diagram illustrating the different categories of users 60 who can interact with the system 100. A user 60 can be a consumer 62 who ingests the nutraceutical 80, a representative 64 acting on behalf of the consumer 62 such as a family member or care taker, a provider 66 such as a physician, nurse, or physician assistant, and an administrator 68 who acts on behalf of the business operating the system 100. Different embodiments of the system 100 can include different capabilities for different users 60 to interact through use of the system 100. For example, the system 100 can be configured to authorize a provider 66 to impact the process by which the application 373 selectively generates outputs 690 such as a personalized recipe 693 from the inputs 610 that include various health attributes 640.

Consumers 62 of the personalized nutraceutical 81 are often human beings, but the system 100 can be used to benefit a wide range of animals and even plants. Whether animals are used for livestock on farms, are beloved family pets, or animals serving very specific purposes such as racehorses, guide dogs, etc. such animals can benefit from customized nutraceuticals 81 that enhance their health and well being.

C. Nutraceutical Products

FIG. 3*c* is a block diagram illustrating different examples of nutraceutical products 80 and their doses. Nutraceuticals 80 can be in a liquid form 82 that are capable of being sprayed 84. Nutraceuticals 80 can be produced in specific doses 86. The quantity of doses 86 can be part of the customization/personalization process of the system 100. Personalized nutraceuticals 81 can also be produced in the form of powders 88.

D. Containers

Figures 3D, 3E:
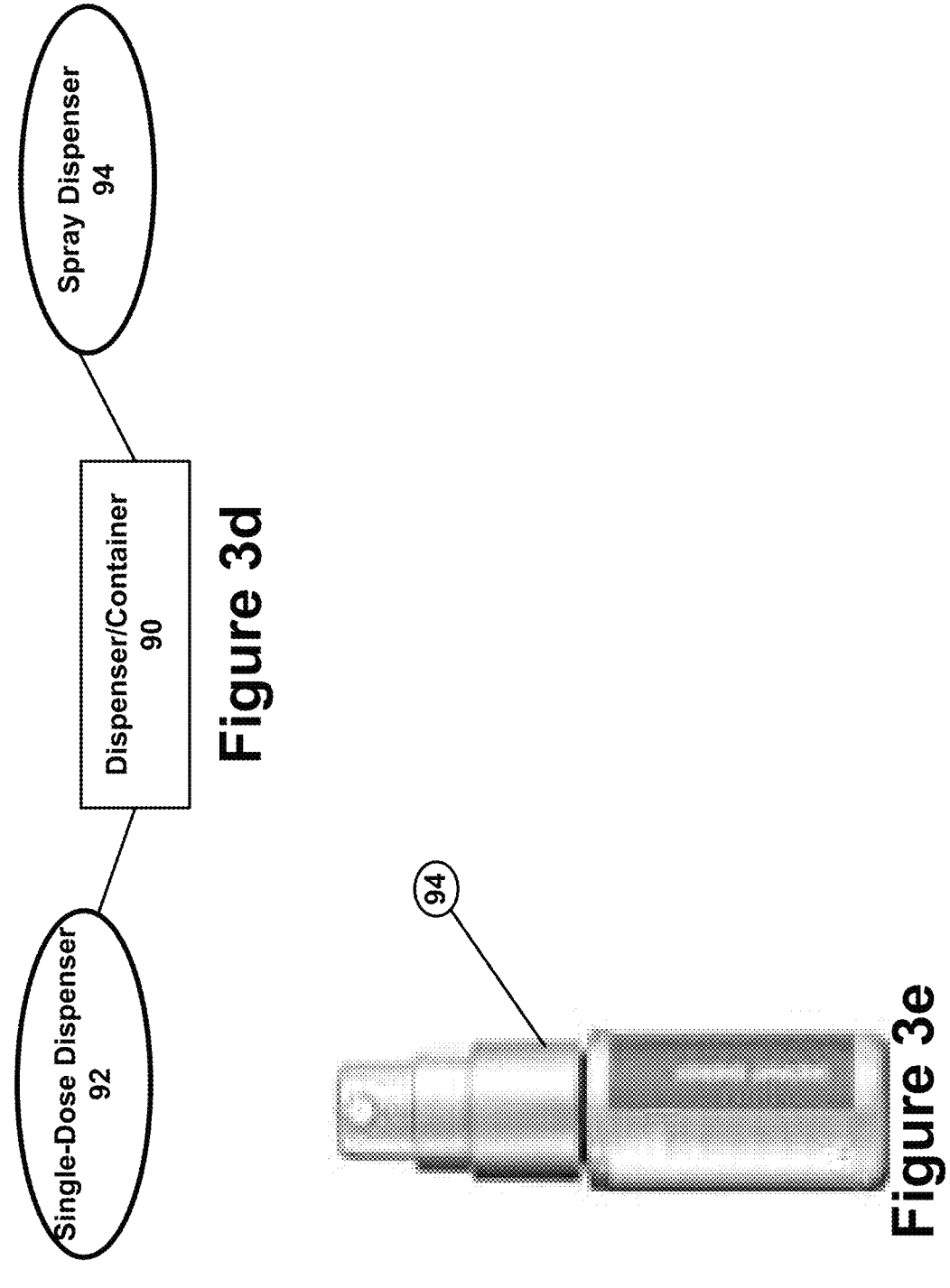
FIG. 3d is a block diagram illustrating different examples of dispensers/containers for holding, dispensing, and using nutraceutical products.
FIG. 3e is a block diagram illustrating an example of a spray dispenser, including potentially a single-dose dispenser.

FIG. 3*d* is a block diagram illustrating different examples of dispensers/containers 90 for holding, dispensing, and using nutraceutical products 80. Some embodiments of the system 100 will use spray dispensers 94 to hold and distribute personalized nutraceuticals 81. In many embodiments, the personalized nutraceuticals 81 will be distributed in the form of a single-dose dispenser 92. FIG. 3*e* is a block diagram illustrating an example of a spray dispenser 94 that can be a single-dose dispenser 92.

E. Types of Computers

Figure 3F:
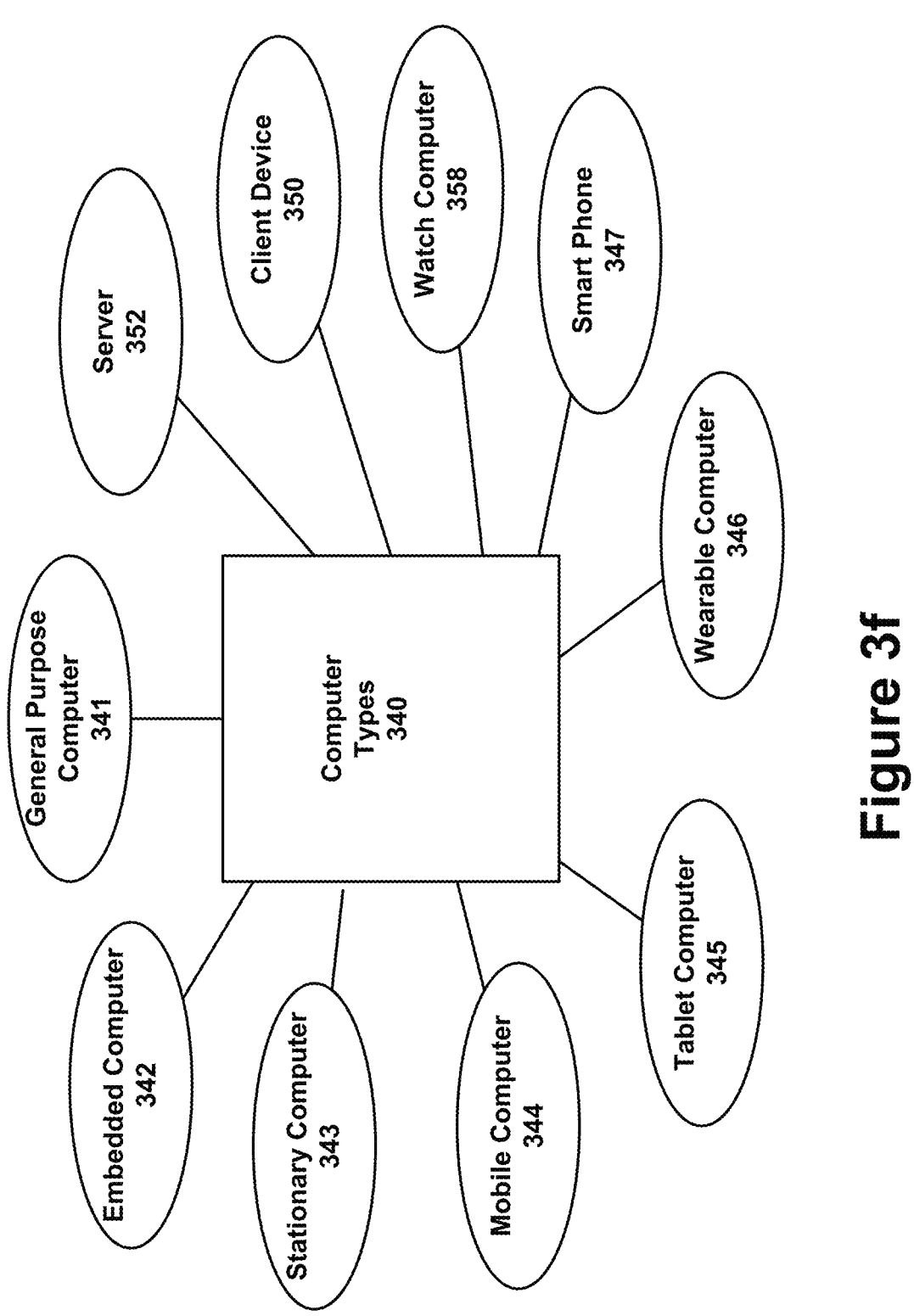
FIG. 3f is a block diagram illustrating different examples of computer types.

FIG. 3*f* is a block diagram illustrating different examples of computer types. 340 that can be incorporated into the system 100. As discussed above, the user 60 uses some type of computer 330 to interact with the system 100, some type of computer 330 is used to create personalized recipes 693, and some type of computer 330 is used as part of the production assembly 500 to actually produce the personalized nutraceutical 81.

Examples of computer types 340 include general purpose computers 341 and embedded computers 342, servers 352 and client devices 350, stationary computers 343 as well as mobile computers 344. Examples of mobile computers 344 can include smart phones 347, tablet computers 345, and wearable computers 346.

Different computer types 340 are more likely to be used to perform different functions within the system 100. Client devices 350 such as mobile computers 344 are more likely to serve as the interface between users 60 and the system 100. Servers 352 across networks 330 are more likely to be used to house the application 373 and data 600 used to create personalized recipes 693. The production assembly 500 is more likely to rely on embedded computers 342 to control manufacturing components within the production assembly 500 in an automated way.

F. Computer Components

Figure 3G:
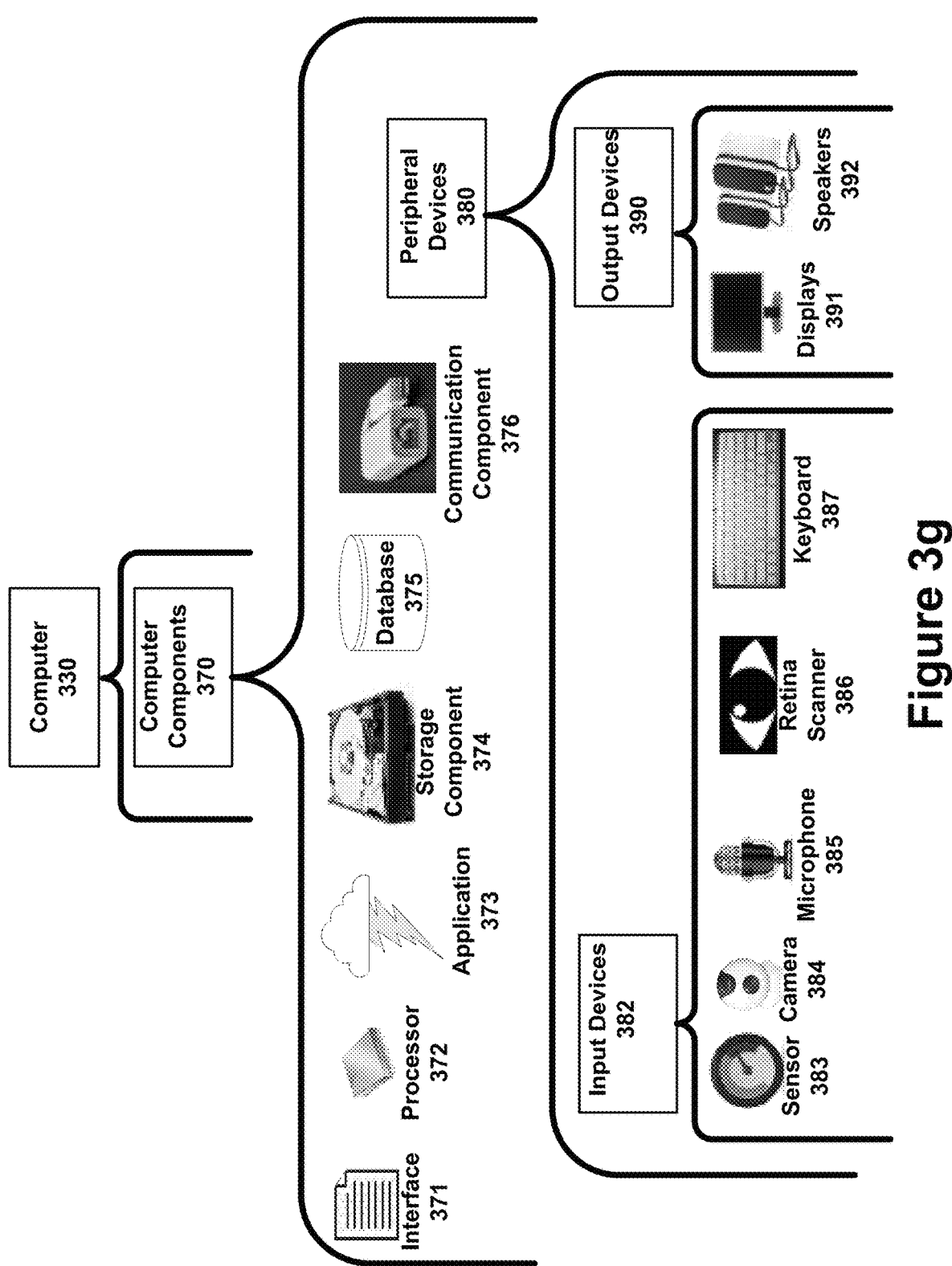
FIG. 3g is a hierarchy diagram illustrating different examples of computer components, peripheral devices, input devices, and output devices.

FIG. 3*g* is a hierarchy diagram illustrating different examples of computer components 370, peripheral devices 380, input devices 382, and output devices 390.

As illustrated in the Figure, a computer 330 is itself comprised of various computer components 370, such as an interface 371, a processor 372, an application 373 that applies the algorithms for selectively modify recipes 692, storage components 374 for storing data 600, databases 375, communication components 376 and peripheral devices 380. Peripheral devices 380 can include input devices 382 such as sensors 383, cameras 384, microphones 385, retina scanners 386, keyboards 387, and other means for receiving inputs 610. Peripheral devices 380 can also include output devices 390 such as display monitors 391, speakers 392, printers, and other similar devices.

G. Data

Figure 3H:
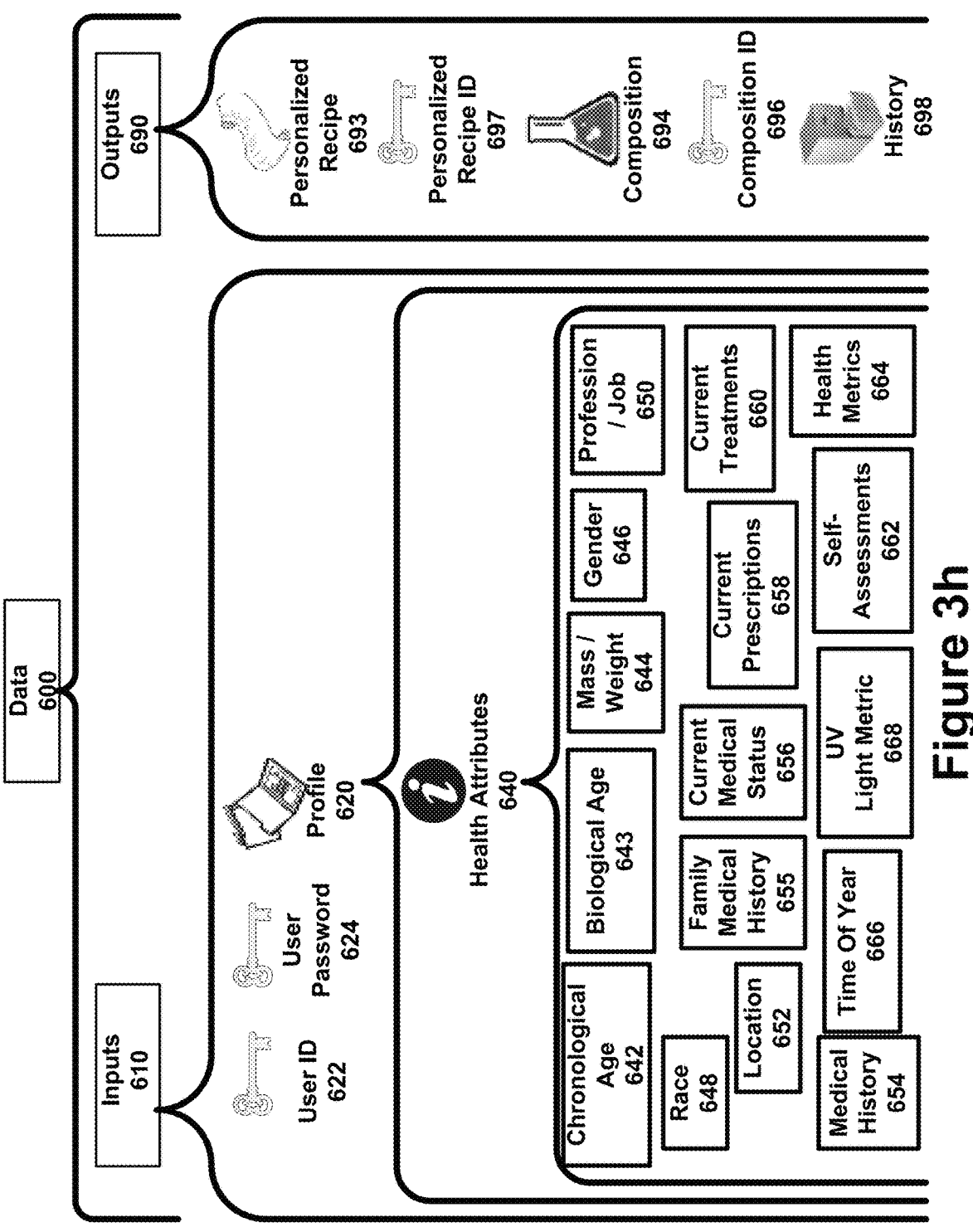
FIG. 3h is a hierarchy diagram illustrating different examples of data, including the various inputs and outputs of the system. All of the processing in FIG. 3h can be subject to the feedback loop in FIG. 1e.

FIG. 3*h* is a hierarchy diagram illustrating different examples of data 600, including the various inputs 610 and outputs 690 of the system 100.

Inputs 610 used by the system 100 can include user IDs 622, user passwords 624, and user profiles 620, which can be comprised of a wide variety of health attributes 640 such as chronological age 642, biological age 643, mass/weight 644, gender 646, race 648, profession/job 650, location 652, family medical history 655, current medical status 656, current prescriptions 658, current treatments 660, medical history 654, time of year 666, UV light metric 668, self-assessments 662, health metrics 664, and other characteristics.

Outputs 690 can include personalized recipes 693, personalized recipe IDs 697, compositions 694, composition IDs 696, and history 698.

VI. Process Flow Views

The system 100 can be implemented in a variety of different ways to perform a variety of different methods 900 of operation.

A. Example #1

Figure 4C:
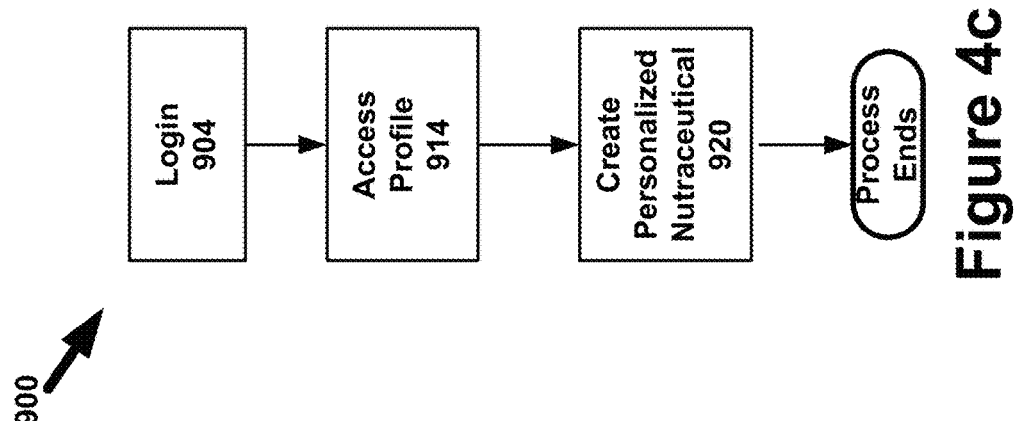
FIG. 4c is a flow chart diagram illustrating an example of a process performed by a user to create a personalized nutraceutical product.
Figure 4B:
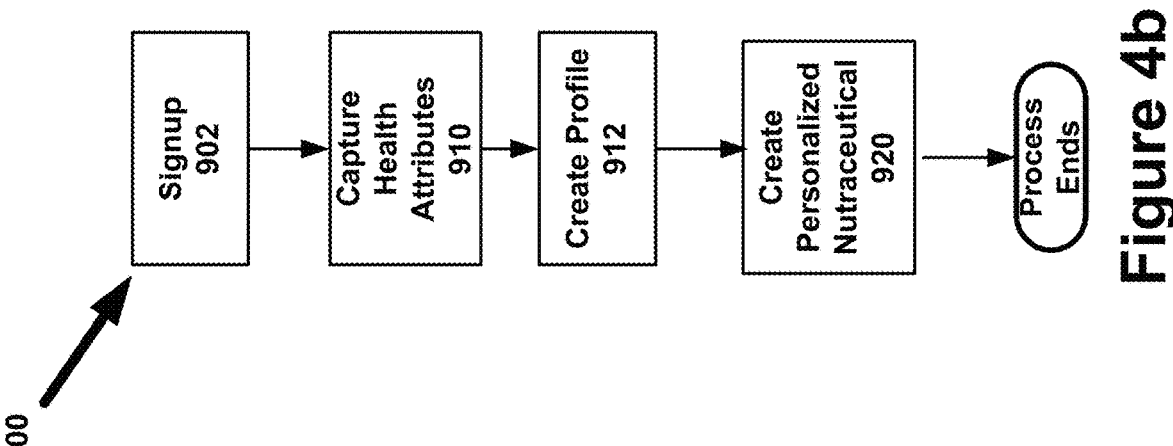
FIG. 4b is a flow chart diagram illustrating an example of a process performed by a user to create a personalized nutraceutical product.
Figure 4A:
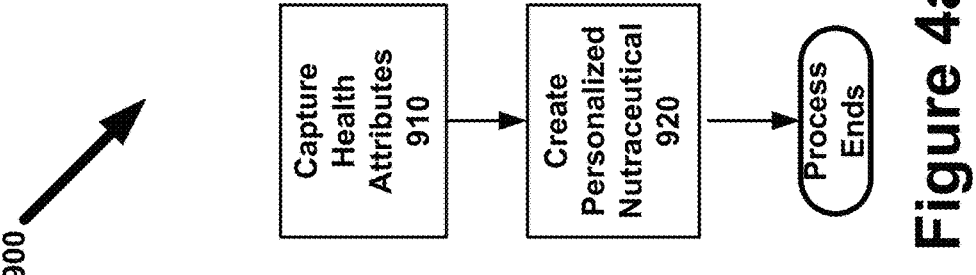
FIG. 4a is a flow chart diagram illustrating an example of a process for creating a personalized nutraceutical.

FIG. 4*a* is a flow chart diagram illustrating an example of a process for creating a personalized nutraceutical 81.

At 910, health attributes 640 of the consumer 62 are captured by the system 100. This can be done with each interaction 70 by the user 60, or alternatively, can be done one time, stored for future access, and selectively updated in the future. The capturing of health attributes 640 can also include using the captured health attributes 640 to derive other health attributes 640. By way of example, the system 100 could derive a biological age 643 (in contrast to the chronological age 642) of the consumer 62 using the data 600 available to the system 100.

At 920, those attributes 640 are used as inputs to the application 373 to create a personalized nutraceutical 81.

B. Example #2

FIG. 4*b* is a flow chart diagram illustrating an example of a process performed by a user 60 to create a personalized nutraceutical product 81.

At 902, the user 60 signs up on the system 100 and the system 100 creates an account for the user 60.

At 910, the system 100 receives/captures health attributes 640 for the consumer 62.

At 912, a profile 912 is created and stored.

At 920, those attributes 640 are used as inputs to the application 373 to create a personalized nutraceutical 81.

C. Example #3

FIG. 4*c* is a flow chart diagram illustrating an example of a process performed by a user 60 to create a personalized nutraceutical product 81.

At 904, the user 60 logs in to the system 100.

At 914, the profile 620 for the applicable user 60 is accessed

At 920, those attributes 640 are used as inputs to the application 373 to create a personalized nutraceutical 81.

D. Example #4

Figure 4E:
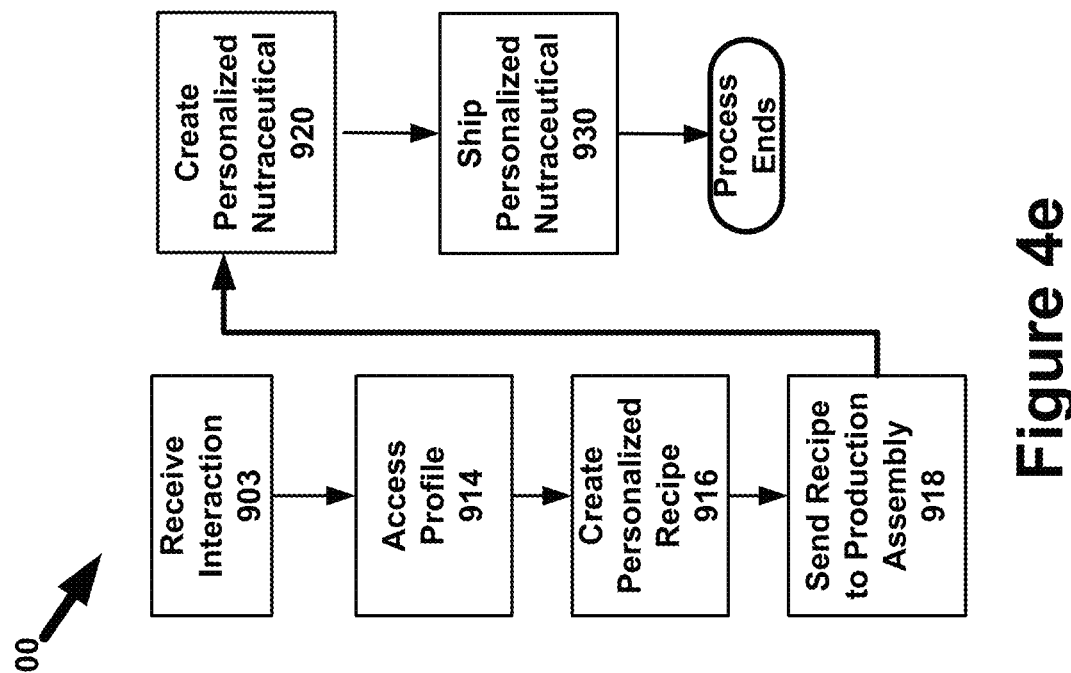
FIG. 4e is a flow chart diagram illustrating an example of a process for an IT system to create a personalized nutraceutical product after receiving an interaction from a user.
Figure 4D:
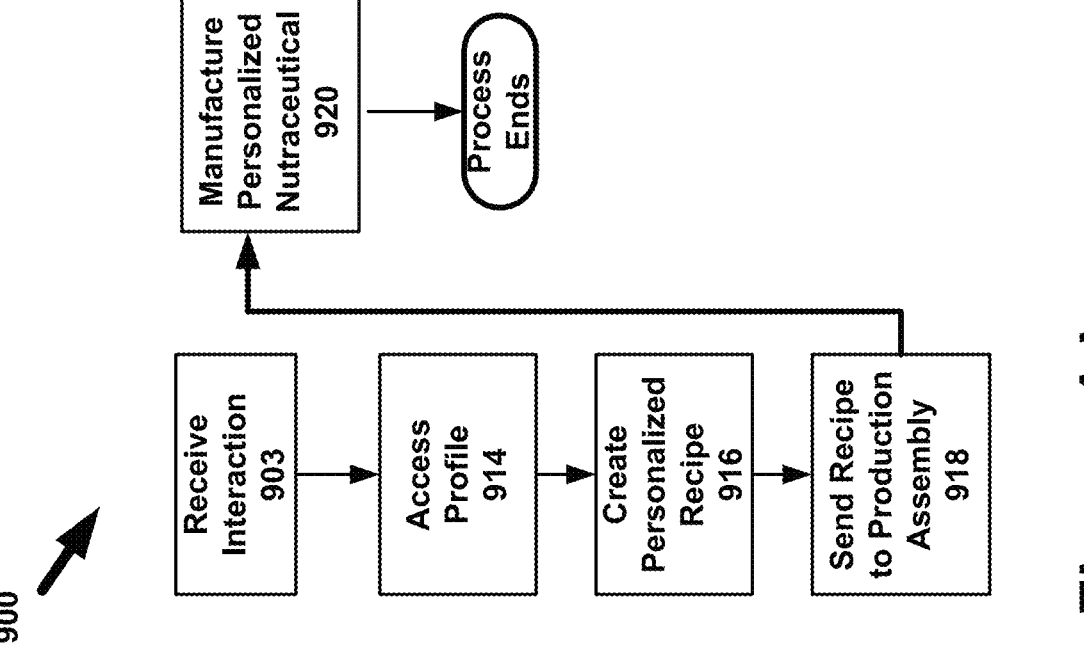
FIG. 4d is a flow chart diagram illustrating an example of a process for an IT system to create a personalized nutraceutical product after receiving an interaction from a user.

FIG. 4*d* is a flow chart diagram illustrating an example of a process for an IT system 100 to create a personalized nutraceutical product after receiving an interaction from a user.

At 903 the interaction 70 is received from the user 60 by the system 100.

At 914, the profile 620 for the applicable user 60 is accessed to access the health attributes 640.

At 916, a personalized recipe 693 is created by the application 373.

At 918, the personalized recipe 693 is sent to the production assembly 500.

At 920, the personalized nutraceutical 81 is produced.

E. Example #5

FIG. 4*e* is a flow chart diagram illustrating an example of a process for an IT system to create a personalized nutraceutical product 81 after receiving an interaction 70 from a user 60.

At 903 the interaction 70 is received from the user 60 by the system 100.

At 914, the profile 620 for the applicable user 60 is accessed to access the health attributes 640.

At 916, a personalized recipe 693 is created by the application 373.

At 918, the personalized recipe 693 is sent to the production assembly 500.

At 920, the personalized nutraceutical 81 is produced.

At 990, the personalized nutraceutical 81 is shipped to the consumer 62.

E. Example #5

Figure 4G:
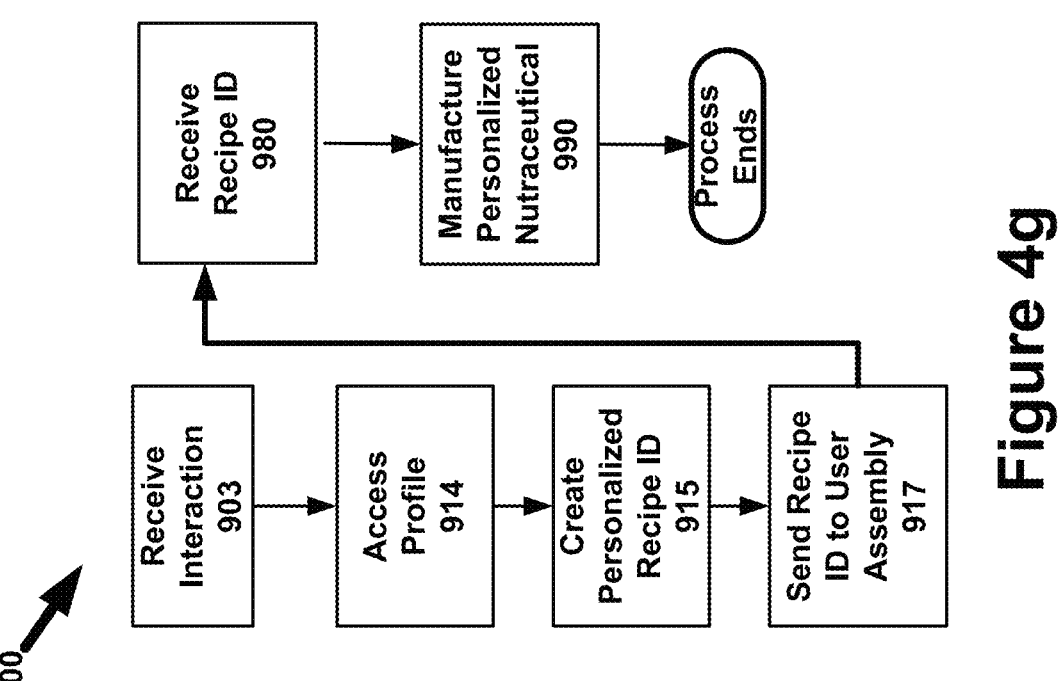
FIG. 4g is a flow chart diagram illustrating an example of a process similar to the process of FIG. 4f, where the nutraceutical product is manufactured at a location remote from the IT components of the system.
Figure 4F:
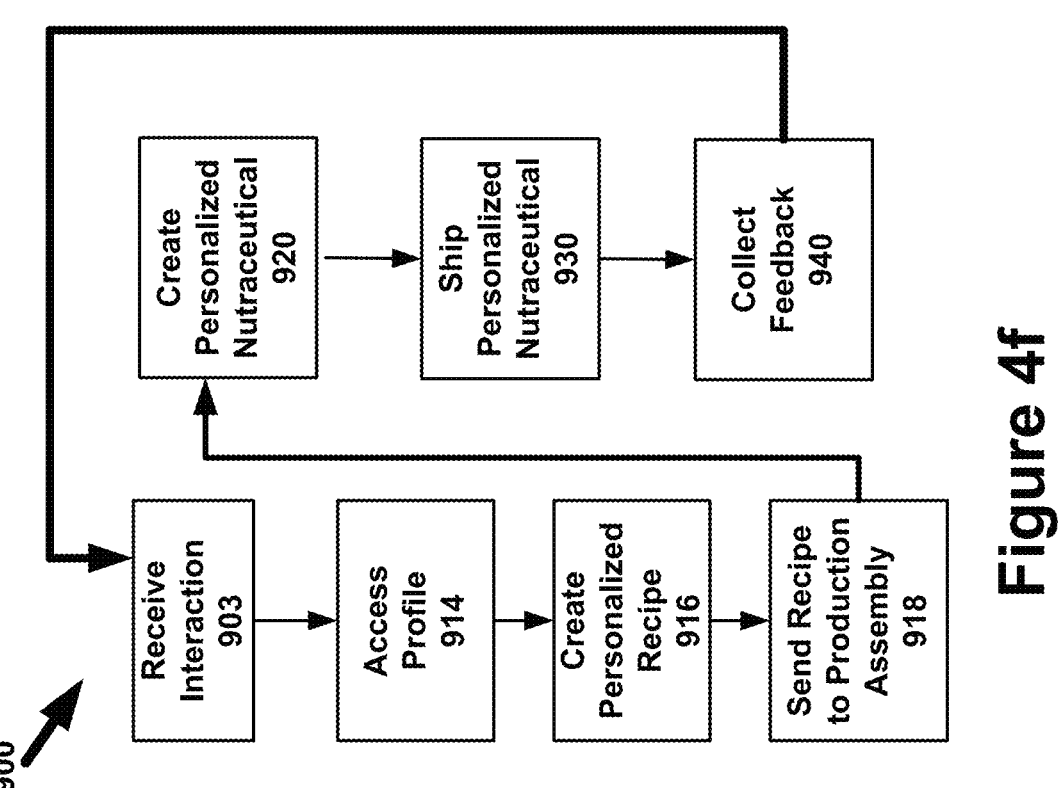
FIG. 4f is a flow chart diagram illustrating an example of a process for an IT system to create a personalized nutraceutical product after receiving an interaction from a user.

FIG. 4*f* is a flow chart diagram illustrating an example of a process for an system 100 to create a personalized nutraceutical product 81 after receiving an interaction 70 from a user 62.

At 903 the interaction 70 is received from the user 60 by the system 100.

At 914, the profile 620 for the applicable user 60 is accessed to access the health attributes 640.

At 915, a personalized recipe 693 and a personalized recipe ID 697 are created by the application 373.

At 917, the personalized recipe ID 697 is sent to the production assembly 500.

At 980, the personalized recipe ID 697 is received by the production assembly 500.

At 990, the personalized nutraceutical 81 is manufactured and shipped to the consumer 62.

F. Example #6

FIG. 4*g* is a flow chart diagram illustrating an example of a process for system 100 to create a personalized nutraceutical 81 similar to the process of FIG. 4*f*, except that the actual nutraceutical 81 is manufactured with a production assembly at the location of the user 60.

VII. Additional Input-Output Diagrams

The system 100 can be implemented in a wide variety of different configurations. At its core is a recipe computer 330 used to create the personalized recipe 693 and a production assembly 500 to physically manufacture a personalized nutraceutical 81 from the personalized recipe 693.

Figure 5A:
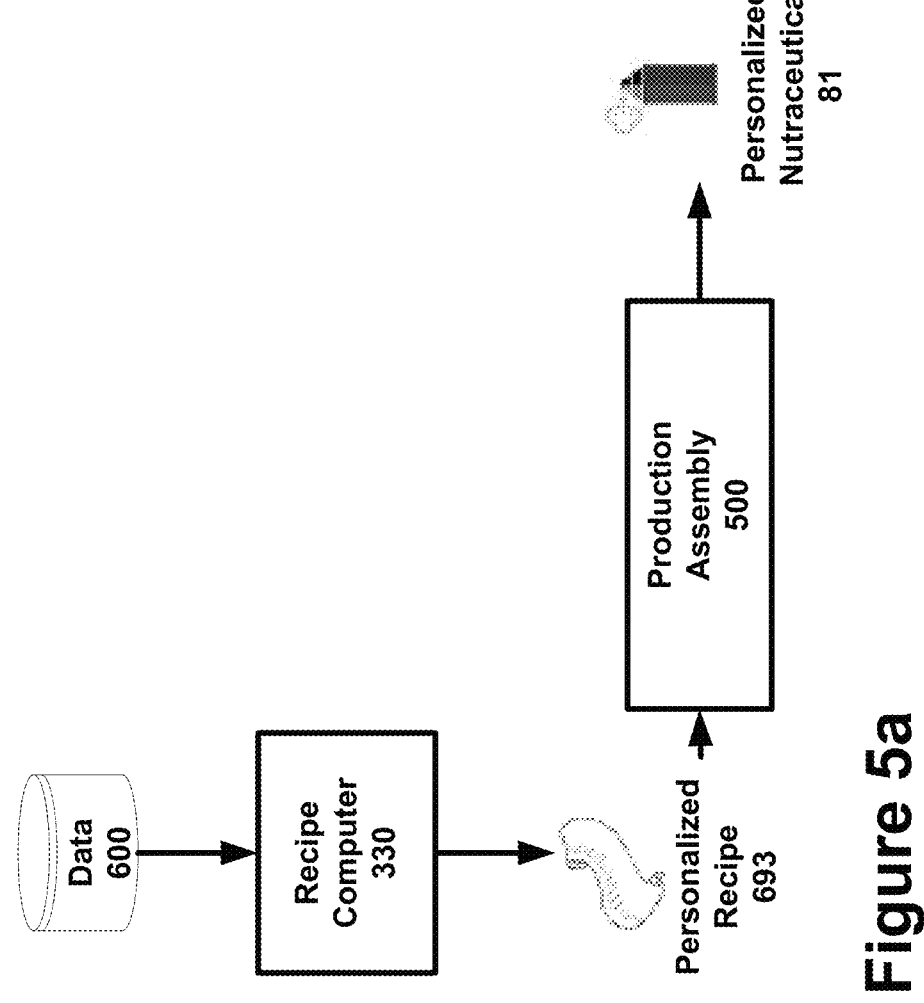
FIG. 5a is a block diagram of the system illustrating an example of the inputs and outputs of the recipe computer and the production assembly.

FIG. 5*a* is a block diagram of the system 100 illustrating an example of the inputs and outputs of the recipe computer 330 and the production assembly 500. The creation of the personalized recipe 693 by the recipe computer 330 can be selectively influenced by any data 600 to which the system

100 has access to. An entire library of health attributes 640 pertaining to the consumer 62 can be factored into and selectively influence the personalized recipe 693. That includes health attributes 640 constituting self-assessments by the consumer 62, objectively measured health attributes 640 captured through sensor readings 692, and derived health attributes 640 such as the biological age 643 of the consumer 62 that are analytically calculated from other health attributes 640 pertaining to the consumer 62. The personalized recipe 693 can also take into consider the location of consumer 62, the time of year in which the personalized nutraceutical 81 is to be consumed, and other potential attributes. Machine learning can be used to fine tune and optimize the ability of the system 100 to produce useful personalized nutraceuticals 81. Data 600 can be used from a variety of different data sources, such as sensor readings 682, user inputs 684, third-party data sources 688, and previously stored data 686. In producing personalized nutraceuticals 81 for different consumers 62 over time, the system 100 can pool the aggregate amount of information for the benefit of all participants in the system 100 without disclosing any personally identifiable information any third parties.

The production assembly 500 can automatically manufacture without human intervention the personalized nutraceutical 81 from the personalized recipe 693 generated by the system 100. The production assembly 500 can include storage containers 510, ingredients 520, mixing containers 530, heating elements 540, stirring elements 560, cooling elements 560, controls 570, and a production computer 330 for automating and monitoring the process.

Figure 5B:
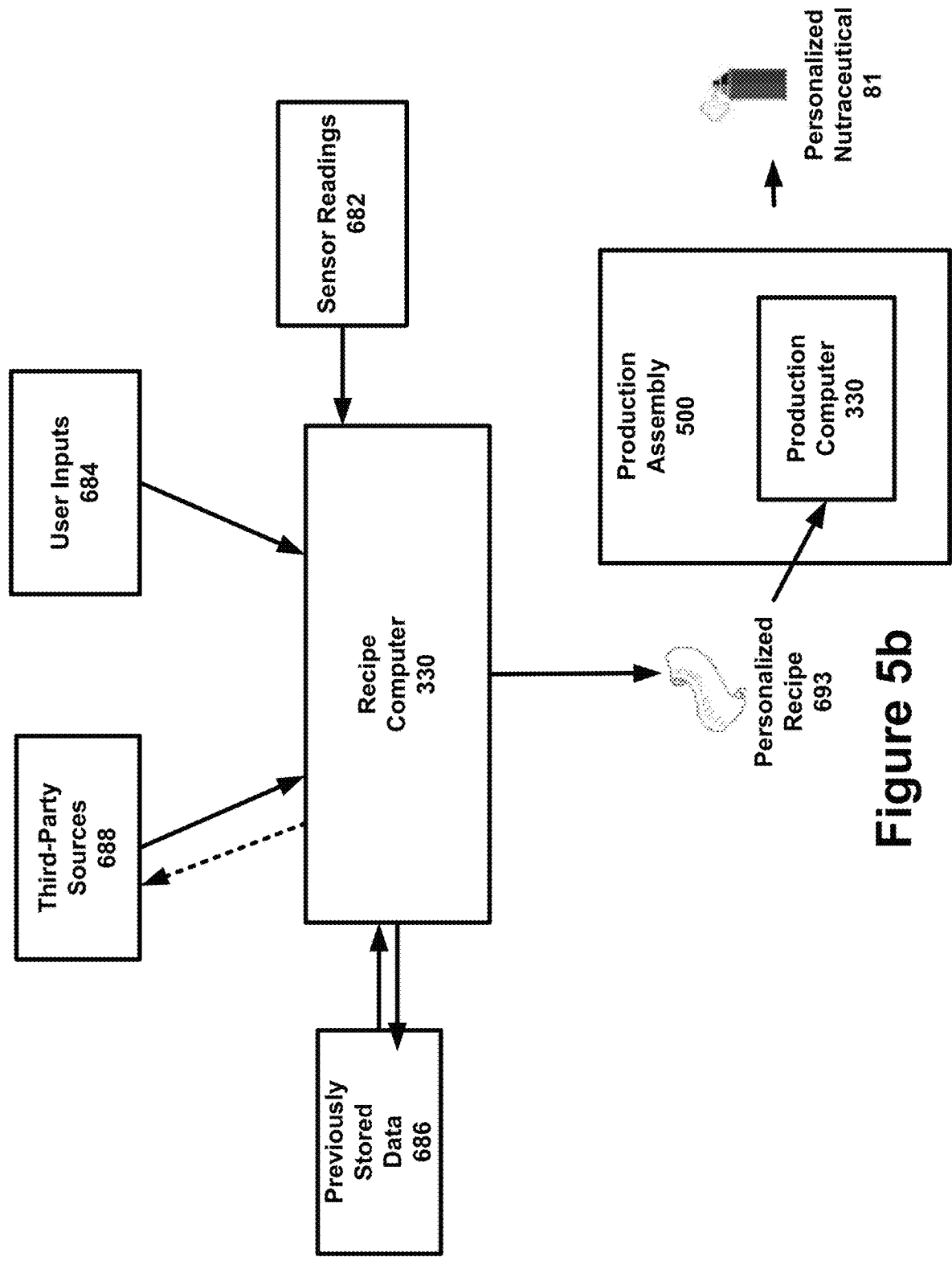
FIG. 5b is a block diagram of the system illustrating an example of the inputs and outputs of the recipe computer and the production assembly.

FIG. 5*b* is a block diagram of the system 100 illustrating an example of the inputs and outputs of the recipe computer 330 and the production assembly 500. Unlike FIG. 5*a*, FIG. 5*b* illustrates an array of data sources, such as previously stored data 686, third party sources 688, user inputs 684, and sensor readings 682. In some instances the exchange of data 600 can be a two way process, as new data 600 created by the system 100 can become previously stored data 686 for future activities by the system 100. Similarly, the exchange with third party sources 688 can be two-way, to facilitate the sharing of information with the system 100. As illustrated in FIG. 5*b*, many embodiments of the production assembly 500 will include a production computer 330 that is separate from the recipe computer 330.

Figure 5C:
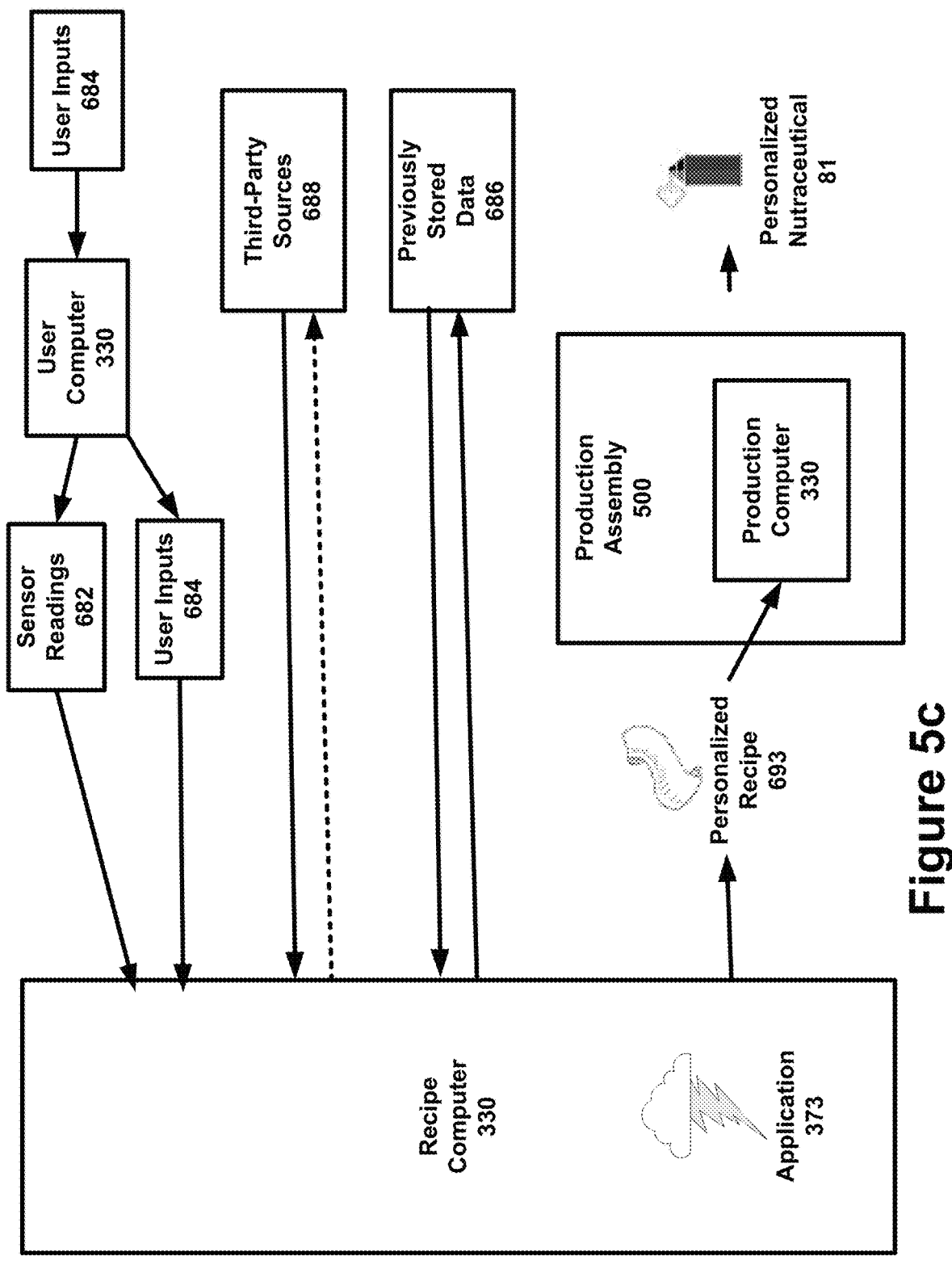
FIG. 5c is a block diagram of the system illustrating an example of the inputs and outputs of the user computer, the recipe computer, and the production assembly.

FIG. 5*c* is a block diagram of the system 100 illustrating an example of the inputs and outputs of the user computer 330, the recipe computer 330, and the production assembly 500. In many embodiments, the user computer 330, recipe computer 330, and production computer 330 are each separate and distinct components of the system 100. The user computer 330 can capture user instructions and information in the form of user inputs 684 and sensor readings 682 captured by the user computer 330, which can be a ubiquitous consumer electronics device such as a smart phone, tablet, or even a wearable device such as a smart watch.

VIII. Alternative Embodiments

Many features and inventive aspects of the system 100 are illustrated in the Figures which are described above. However, no patent application can fully disclose through the use of text descriptions or graphical illustrations, all of the potential embodiments of an invention. In accordance with the provisions of the patent statutes, the principles and modes of operation of the system 100 are explained and illustrated with respect to certain preferred embodiments.

However, it must be understood that the components, configurations, and methods described above and below may be practiced otherwise than is specifically explained and illustrated without departing from its spirit or scope. Each of the various elements described in the glossary set forth in Table 1 above can be implemented in a variety of different ways while still being part of the spirit and scope of the invention.

The invention claimed is:

1. A system (100) for producing a personalized nutraceutical (81) tailored to a specified consumer (62), said system (100) comprising:

a recipe computer (330) for automatically creating a personalized recipe (693) for the specified consumer (620) from at least a subset of a plurality of universal ingredients (520), wherein said personalized recipe (693) for the specified consumer (62) is selectively influenced by a plurality of health attributes (640) associated with the specified consumer (62);

a database (375) accessible through said recipe computer (330), wherein said database (375) stores said plurality of health attributes (640) pertaining to the specified consumer (62); and a production assembly (500), said production assembly (500) including said plurality of universal ingredients (520) stored in a plurality of storage containers (510), said production assembly (500) being configured to manufacture said personalized nutraceutical (81) using at least said subset of said plurality of universal ingredients (520), wherein said production assembly (500) comprises a production computer (330) that controls an operation of said production assembly (500) for an implementation of said personalized recipe (693) to produce said personalized nutraceutical (81) based on said personalized recipe (693).

2. The system (100) of claim 1, wherein the specified consumer (62) is not a human being.

3. The system (100) of claim 1, wherein said personalized nutraceutical (81) is a powder (88).

4. The system (100) of claim 1, wherein said plurality of health attributes (640) include a biological age (643) that is derived from at least a subset of said plurality of health attributes (640) by said recipe computer (330).

5. The system (100) of claim 4, wherein said plurality of health attributes (640) include a chronological age (642) that is different from said biological age (643).

6. The system (100) of claim 1, wherein said production computer (330) is also said recipe computer (330).

7. The system (100) of claim 1, further comprising a user computer (330) that is configured for receiving an interaction (70) for said personalized nutraceutical (81) on behalf of the specified consumer (62).

8. The system (100) of claim 7, wherein said user computer (330) communicates a user input (684) to said recipe computer (330), wherein said recipe computer (330) uses an application (373) configured to create said personalized recipe (693), wherein the personalized recipe (693) is also selectively influenced by said user input (684).

9. The system (100) of claim 8, wherein said user computer (330) communicates a sensor reading (682) relating to the specified consumer (92), and wherein said personalized recipe (693) from said recipe computer (330) is selectively influenced by said sensor reading (682).

10. The system (100) of claim 8, wherein said personalized recipe (693) created by said recipe computer (330) is selectively influenced by a third-party data source (688).

11. The system (100) of claim 1, wherein said personalized nutraceutical (81) is a liquid (82) and wherein said recipe computer (330) creates said personalized recipe (693) from a plurality of said plurality of health attributes (640) without human intervention.

12. The system (100) of claim 1, said production assembly (500) further comprising a dispenser (90) wherein said personalized nutraceutical (81) is packaged in said dispenser (90) by said production assembly (500), wherein said dispenser (90) that is a spray dispenser (94) and a single-dose dispenser (92).

13. The system (100) of claim 1, wherein said personalized recipe (693) is specific to the specified consumer (62) and a particular period of time, and wherein said personalized recipe (693) is selectively influenced by a feedback datum (600) relating to a past recipe (693).

14. The system (100) of claim 1, said system (100) further comprising a user computer (330), wherein a user (60) uses said user computer (330) to initiate an interaction (70) with the system (100) to produce said personalized nutraceutical (81) for the specified consumer (62) who is not the user (60).

15. The system (100) of claim 1, wherein said personalized recipe (693) is created without human intervention and wherein said personalized nutraceutical (81) is manufactured without human intervention.

16. The system (100) of claim 1, said system (100) further comprising a user computer (330), wherein said user computer (330) is a wearable computer (346) that includes a sensor (383) for capturing at least one of said plurality of health attributes (640).

17. The system (100) of claim 1, wherein said recipe computer (330) uses machine learning technology to create said personalized recipe (693).

18. The system (100) of claim 1, wherein said recipe computer (330) can create more than 1,000,000 variations of said personalized recipe (693).

19. A system (100) for producing a personalized nutraceutical (81) tailored to a specified consumer (62), said system (100) comprising:

a plurality of computers (330), said plurality of computers including:

a user computer (330) for receiving an interaction (70) on behalf of the specified consumer (62);

a recipe computer (330) for automatically creating a personalized recipe (693) without human intervention for the specified consumer (620) from at least a subset of a plurality of universal ingredients (520), wherein said personalized recipe (693) for the specified consumer (62) is selectively influenced by a plurality of health attributes (640) associated with the specified consumer (62) and said interaction (70) from said user computer (330); and a production computer (330) for automatically manufacturing said personalized nutraceutical (81) using at least said subset of said plurality of universal ingredients (520) within a production assembly (500) and said personalized recipe (693) from said recipe computer (330);

a database (375) accessible through said recipe computer (330), wherein said database (375) stores said plurality of health attributes (640) pertaining to the specified consumer (62);

a network (310) connecting said plurality of computers (330);

wherein said production assembly (500) including said plurality of universal ingredients (520) stored in a plurality of storage containers (510), said production assembly (500) being configured to manufacture said personalized nutraceutical (81) using at least said subset of said plurality of universal ingredients (520), wherein said production computer (330) controls an operation of said production assembly (500) for an implementation of said personalized recipe (693) to produce said personalized nutraceutical (81) based on said personalized recipe (693).

20. A method (900) for producing a personalized nutraceutical (81) for a specified consumer (62), said method comprising:

creating (916) a personalized recipe (693) through an operation of an application (373) running on a recipe computer (330) wherein the operation of said application (373) is selectively influenced by a plurality of inputs (610), said plurality of inputs (610) including at least a subset of a plurality of health attributes (640), wherein said plurality of health attributes (640) include a chronological age (642) and a biological age (643); and manufacturing (920) said personalized nutraceutical (81) in accordance with said personalized recipe (393) using a production assembly (500).

21. The method (900) of claim 20 further comprising:

distributing said personalized nutraceutical (81) in a single-dose dispenser.

* * * * *